(12) United States Patent
Cadwell et al.

(10) Patent No.: US 11,241,297 B2
(45) Date of Patent: Feb. 8, 2022

(54) SYSTEM AND METHOD FOR HIGH DENSITY ELECTRODE MANAGEMENT

(71) Applicant: Cadwell Laboratories, Inc., Kennewick, WA (US)

(72) Inventors: John A. Cadwell, Richland, WA (US); Patrick Scott Jensen, West Richland, WA (US); Brandon Vazquez, Pasco, WA (US); Wayne Dearing, Kennewick, WA (US)

(*) Notice: Subject to any disclaimer, the term of this patent is extended or adjusted under 35 U.S.C. 154(b) by 185 days.

(21) Appl. No.: 16/698,879

(22) Filed: Nov. 27, 2019

(65) Prior Publication Data
US 2020/0093566 A1 Mar. 26, 2020

Related U.S. Application Data

(63) Continuation-in-part of application No. 16/267,689, filed on Feb. 5, 2019, which is a continuation of
(Continued)

(51) Int. Cl.
*A61B 90/98* (2016.01)
*A61B 90/96* (2016.01)
(Continued)

(52) U.S. Cl.
CPC .......... *A61B 90/98* (2016.02); *A61B 5/24* (2021.01); *A61B 5/291* (2021.01); *A61B 5/296* (2021.01);
(Continued)

(58) Field of Classification Search
None
See application file for complete search history.

(56) References Cited

U.S. PATENT DOCUMENTS 6,236,874 B1 5/2001 Devlin
6,805,668 B1 10/2004 Cadwell
(Continued)

FOREIGN PATENT DOCUMENTS

DE 102014008684 A1 1/2016
EP 0863719 A1 9/1998
(Continued)

OTHER PUBLICATIONS

International Search Report for PCT/US2019/063793, dated Feb. 19, 2020.
(Continued)

*Primary Examiner* — Ankit D Tejani
(74) *Attorney, Agent, or Firm* — Novel IP

(57) ABSTRACT

Systems, devices and methods for advanced electrode management in neurological monitoring applications include receiving sockets configured to receive connectors having groups of electrodes. The physician is not required to manually map each electrode with its corresponding input channel. Electrodes are coupled to the corresponding input channels in groups through connectors having a unique identification (ID). The system is configured to read the unique ID of each connector and establish its identity. Based on the ID, the system configures itself to automatically correlate or associate each electrode with its corresponding input channel when the connectors are first inserted into the receiving sockets, and again if the connectors are removed and re-inserted into different positions in the receiving sockets, to insure the electrodes are always mapped to the same input channels.

35 Claims, 19 Drawing Sheets

Related U.S. Application Data application No. 15/376,655, filed on Dec. 12, 2016, now Pat. No. 10,238,467.

(60) Provisional application No. 62/774,042, filed on Nov. 30, 2018.

(51) Int. Cl.
*A61B 5/24* (2021.01)
*A61B 5/291* (2021.01)
*A61B 5/296* (2021.01)
*A61B 5/30* (2021.01)

(52) U.S. Cl.
CPC .............. *A61B 5/303* (2021.01); *A61B 90/96* (2016.02); *A61B 2562/0209* (2013.01); *A61B 2562/046* (2013.01); *A61B 2562/226* (2013.01); *A61B 2562/227* (2013.01)

(56) References Cited

U.S. PATENT DOCUMENTS

| | | |
|---|---|---|
| 6,870,109 B1 | 3/2005 | Villarreal |
| 7,072,521 B1 | 7/2006 | Cadwell |
| 7,230,688 B1 | 6/2007 | Villarreal |
| 7,374,448 B1 | 5/2008 | Jepsen |
| 7,914,350 B1 | 3/2011 | Bozich |
| D670,656 S | 11/2012 | Jepsen |
| 9,155,503 B2 | 10/2015 | Cadwell |
| 9,295,401 B2 | 3/2016 | Cadwell |
| 9,730,634 B2 | 8/2017 | Cadwell |
| 10,238,467 B2 | 3/2019 | Cadwell |
| 2004/0030258 A1 | 2/2004 | Williams |
| 2007/0202005 A1 | 8/2007 | Maschke |
| 2008/0312520 A1 | 12/2008 | Rowlandson |
| 2009/0196471 A1 | 8/2009 | Goetz |
| 2010/0113898 A1 | 5/2010 | Kim |
| 2012/0003862 A1 | 1/2012 | Newman |
| 2013/0012880 A1 | 1/2013 | Blomquist |
| 2014/0121555 A1 | 5/2014 | Scott |
| 2014/0275926 A1 | 9/2014 | Scott |
| 2015/0230749 A1 | 8/2015 | Gharib |
| 2015/0351643 A1* | 12/2015 | Edwards ............ A61B 5/02141 600/301 |
| 2015/0372433 A1 | 12/2015 | Lisogurski |
| 2016/0000382 A1 | 1/2016 | Jain |
| 2016/0174861 A1 | 6/2016 | Cadwell |
| 2016/0328991 A1 | 11/2016 | Simpson |
| 2018/0161123 A1 | 6/2018 | Cadwell |

FOREIGN PATENT DOCUMENTS

| | | |
|---|---|---|
| EP | 1182965 B1 | 3/2002 |
| EP | 2173238 A2 | 4/2010 |
| WO | 2016028822 A1 | 2/2016 |

OTHER PUBLICATIONS

International Search Report for PCT/US2017/062559, dated Jan. 26, 2018.

* cited by examiner

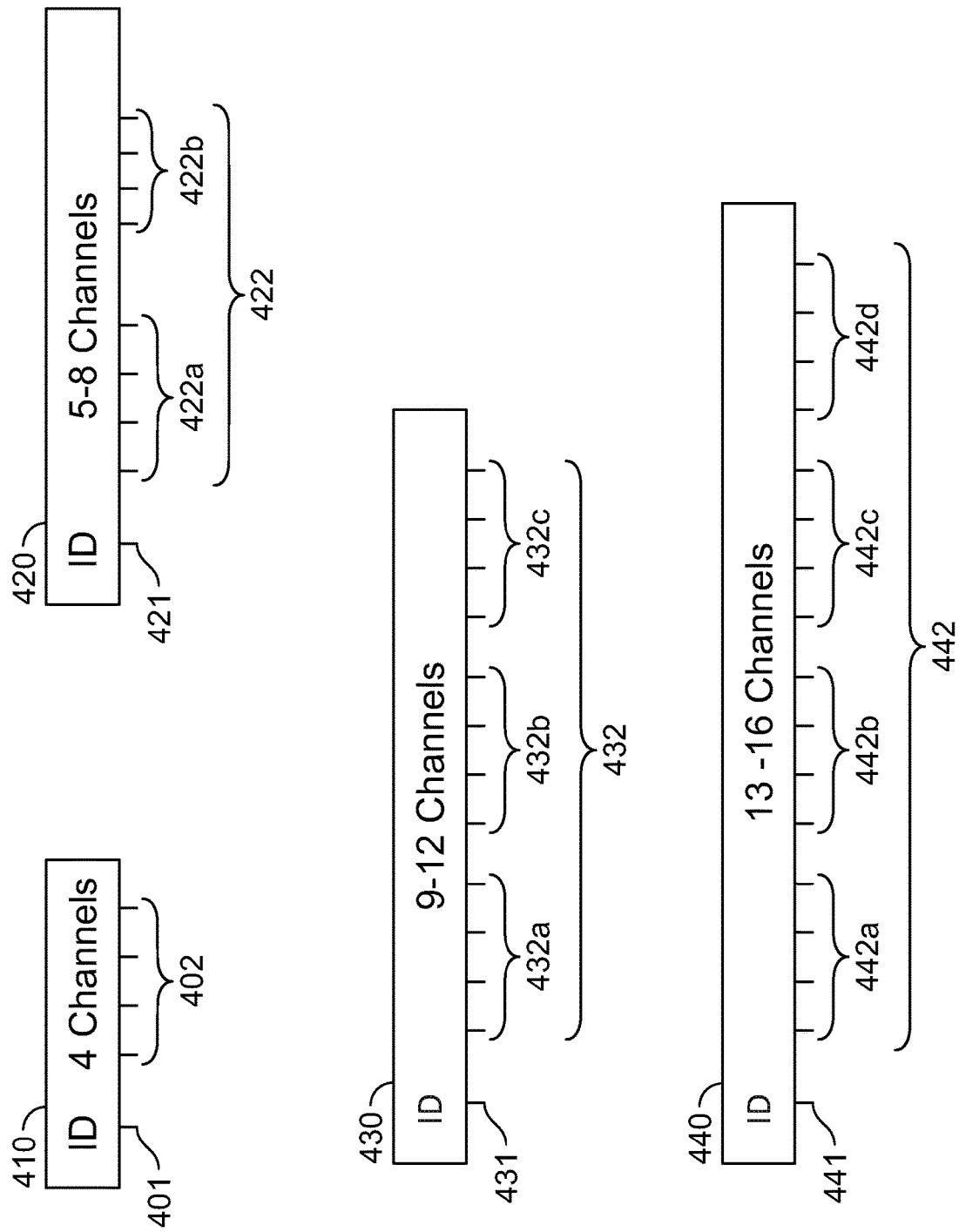

SYSTEM AND METHOD FOR HIGH DENSITY ELECTRODE MANAGEMENT

CROSS-REFERENCE

The present application relies on U.S. Patent Provisional Application No. 62/774,042, entitled "System and Method for High Density Electrode Management" and filed on Nov. 30, 2018, which is herein incorporated by reference in its entirety.

In addition, the present application is a continuation-in-part application of U.S. patent application Ser. No. 16/267,689, entitled "System and Method for High Density Electrode Management" and filed on Feb. 5, 2019, which, in turn, is a continuation of U.S. patent application Ser. No. 15/376,655, entitled "System and Method for High Density Electrode Management", filed on Dec. 12, 2016, and issued as U.S. Pat. No. 10,238,467 on Mar. 26, 2019, all of which are herein incorporated by reference in their entirety.

FIELD

The present specification generally relates to the field of neuro-monitoring applications and more specifically to a system and method for managing a large number of electrodes in such applications.

BACKGROUND

Several medical procedures involve deploying multiple sensors on the human body for the recording and monitoring of data required for patient care. Information, such as vital health parameters, cardiac activity, bio-chemical activity, electrical activity in the brain, gastric activity and physiological data, is usually recorded through on-body or implanted sensors/electrodes which are controlled through a wired or wireless link. Typical patient monitoring systems comprise a control unit connected through a wire to one or more electrodes coupled to the specific body parts of the patient. In some applications, such as with pulse oximeter or EKG (electrocardiograph) devices, the electrodes coupled to the body are easily managed as there are not too many (fewer number of electrodes). However, with applications that require a large number of electrodes to be coupled to the human body, the overall set up, placement and management of electrodes is a cumbersome process.

Neuromonitoring includes the use of electrophysiological methods, such as electroencephalography (EEG), electromyography (EMG), and evoked potentials, to monitor the functional integrity of certain neural structures (e.g., nerves, spinal cord and parts of the brain) during surgery. The purpose of neuromonitoring is to reduce the risk to the patient of iatrogenic damage to the nervous system, and/or to provide functional guidance to the surgeon and anesthesiologist. Neurodiagnostics includes the use of electrophysiological methods, such as electroencephalography (EEG), electromyography (EMG), polysomnography (PSG) and evoked potentials, to diagnose the functional integrity of certain neural structures (e.g., nerves, spinal cord and parts of the brain) to assess disease states and determine potential therapy or treatment. Generally, neuromonitoring and neurodiagnostic procedures may involve a large number of electrodes coupled to the human body. For example, in an EEG procedure, the electrodes are used to record and monitor the electrical activity corresponding to various parts of the brain for detection and treatment of various ailments such as epilepsy, sleep disorders and coma. EEG procedures are either non-invasive or invasive. In non-invasive EEG, a number of electrodes are deployed on the human scalp for recording electrical activity in portions of the underlying brain. In invasive EEG, through surgical intervention, the electrodes are placed directly over sections of the brain, in the form of a strip or grid, or are positioned in the deeper areas of the brain, in the form of depth electrodes. Each of these electrodes is coupled to a wire lead which, in turn, is connected to a control unit adapted to receive and transmit electrical signals. The electrical activity pattern captured by various electrodes is analyzed using standard algorithms to localize or spot the portion of brain which is responsible for causing the specific ailment.

While EEG is a stand-alone product and medical discipline, it can be used as a component of neuromonitoring, for example, in the operating room for neuromonitoring during surgery. EEG may also be used in an in-patient setting such as an epilepsy monitoring unit (EMU). In the case of monitoring in an EMU, a patient will undergo surgery to place strip, grid, or depth electrodes on or in the brain and then remain in a hospital room under observation for 7-10 days. During this time, the patient will be taken off of their epilepsy medications and any resulting seizures recorded. This is potentially dangerous to the patient which necessitates constant medical observation. Once the affected area of the brain is identified for removal or treatment, a second surgical procedure is performed to either remove the focal point of the seizures or to implant a device to help stop the seizures.

The number of electrodes in EEG systems typically varies between 21 and 256 and can be over 500. Increasing the number of electrodes in EEG procedures helps decrease the localization error and thus more ably assist the physician to better plan for surgical procedures. Accordingly, advanced EEG systems involve electrode configurations to separately map the electrical activity corresponding to many portions of the brain. However, the overall set up and verification process for these advanced EEG systems becomes more time consuming and error prone as the number of electrodes increases in the EEG procedures.

In neuromonitoring and neurodiagnostics, as each electrode is positioned at a different location to capture the electrical activity in its vicinity, the input recorded from each electrode has to be processed independently. The system is required to recognize the identity of each electrode and accordingly process the input received from that electrode. To achieve this, it is important that each electrode is coupled to the correct input channel in the control unit of the neuromonitoring or neurodiagnostics system. However, in practical scenarios, it is possible that, while connecting a large number of electrodes to respective input channels, the medical care provider connects an electrode to a wrong input channel. This could result in making the entire process faulty. Therefore, in high density electrode configurations, the set up process is time consuming as the connection corresponding to each electrode needs to be separately established and then verified for integrity before starting the procedure. In practice, the time required to set up and verify large numbers of connecting leads prevents following the best practice of checking all electrodes and verifying their integrity before starting the procedure and hence compromises the quality of medical care.

Surgical applications in EEG also use strip, grid and depth electrode arrays (and other electrode geometries) which typically combine multiple unique conductive elements into a pattern placed within a substrate material and then placed in contact with the brain. Lead wires connected to each conductive element are grouped into cables (from 1 to 4 or more depending on the size of the electrode array) attached to the electrode and typically terminate in one connector per cable with each cable containing 4 or more lead wires. Each connector is attached to an adapter with typically 4 or more individual leads, each lead corresponding to a unique element on the electrode, and then to an amplifier that has inputs for each individual channel. However, when a patient is monitored with an EEG system having, for example, 200+ electrodes, even grouping these electrodes results in more than a dozen adapters and the connections corresponding to these adapters needs to be individually verified every time before starting a procedure.

Therefore, the current neuromonitoring and neurodiagnostics medical devices involving a large number of electrodes do not provide an easy and convenient way for physicians to deploy such systems. These systems suffer from significant risk of unreliable measurements due to incorrect connections. There is significant risk of error in deploying such systems. Further, deployment of such systems is time consuming which prevents following the best practices and therefore compromises the quality of medical care.

Devices and systems are required which are convenient to use, do not consume too much time for deployment, and reduce the risk of configuration error. Such devices and systems should automatically recognize the position or identity of various electrodes and associate the electrodes with a specific input channel, thereby not requiring the physician to manually map each electrode with a specific input channel. Such devices would reduce the complexity of the large number of connections, reduce connection errors, and reduce the time to connect and configure the monitoring systems. The devices would also streamline workflow around patient care and system configuration and enhance the serviceability of neuromonitoring and neurodiagnostics products.

SUMMARY

The present specification discloses a system for neuromonitoring comprising: a plurality of electrode groups, wherein each group of the plurality of electrode groups comprises electrodes, wherein each of the electrodes in each group has at least one of a similar monitoring functionality type or a similar deployment location and wherein each of the plurality of electrode groups has at least one electrode group lead; a plurality of connectors, wherein each of the at least one electrode group leads is coupled to at least one connector of the plurality of connectors and wherein each of the electrode group leads and/or each of connectors of the plurality of connectors are electronically associated with a unique identification code; and, a control unit comprising at least one receiving unit configured for receiving the plurality of connectors, wherein the control unit is configured to determine at least one of the unique identification code of each connector of the plurality of connectors or the unique identification code of each of the at least one electrode group leads and to associate each electrode in the plurality of electrode groups with a corresponding input channel in the control unit based on at least one of the unique identification code of each connector or the unique identification code of each of the at least one electrode group leads.

The unique identification code may be in a 128 bit GUID format.

The at least one receiving unit may comprise a plurality of input sockets configured to receive one or more connectors of said plurality of connectors. The one or more connectors may be configured to be coupled to any of the plurality of input sockets of said at least one receiving unit.

Optionally, the control unit is configured to determine at least one of the unique identification code of each connector of the plurality of connectors or the unique identification code of each of the at least one electrode group leads by receiving, via each connector of the plurality of connectors, data indicative of at least one of the unique identification code of each connector of the plurality of connectors or the unique identification code of each of the at least one electrode group leads.

Optionally, the control unit is configured to receive, via each connector of the plurality of connectors, data indicative of at least one of the unique identification code of each connector of the plurality of connectors or the unique identification code of each of the at least one electrode group leads through a direct pin-to-pin electrical pass through.

Optionally, the control unit is configured to determine at least one of the unique identification code of each connector of the plurality of connectors or the unique identification code of each of the at least one electrode group leads by receiving, via at least one connector of the plurality of connectors, data indicative of at least one of the unique identification code of each connector of the plurality of connectors or the unique identification code of each of the at least one electrode group leads.

Optionally, the control unit is configured to receive, via each connector of the plurality of connectors, data indicative of at least one of a production date or authentication data.

Optionally, the control unit is configured to receive, via each connector of the plurality of connectors and through a direct pin-to-pin electrical pass through, data indicative of at least one of a production date of the plurality of connectors or the electrodes or authentication data.

The connector may have a designated output pin which is configured to transmit information related to the unique identification code to said control unit. Data indicative of the unique identification code may be stored in a memory associated with the designated output pin.

Data indicative of the unique identification code may comprise a bar code or a radio frequency code (RFID).

Data indicative of the unique identification code may be stored using at least one pin configured as at least one dip switch comprising at least one resistor.

Optionally, each connector of the plurality of connectors is configured to be inserted in the at least one receiving unit in at least two different orientations.

Optionally, each connector of the plurality of connectors comprises at least two designated output pins, each of which being configured to convey data indicative of the unique identification code and an orientation of a connector of the plurality of connectors. Optionally, the at least two designated output pins are configured to be at different polarities or at different voltage levels to indicate the orientation of the connector of the plurality of connectors. Optionally, a physical position of the at least two designated output pins is different in each of the at least two different orientations.

Optionally, the system further comprises a rigid connector plate, wherein the connector plate comprises a plurality of openings, each opening of the plurality of openings being configured to receive each connector of the plurality of connectors, and wherein each opening of the plurality of openings is separated from an adjacent opening of the plurality of openings by a portion of the connector plate. Optionally, each connector of the plurality of connectors is partially positioned in each opening of the plurality of openings such that a first end of each connector extends outward from a first surface of the connector plate and a second end, opposing the first end, of each connector extends outward from a second surface of the connector plate, wherein the second surface opposes the first surface.

Optionally, the system further comprises a rigid connector plate, wherein the connector plate comprises a plurality of sockets, each socket of the plurality of sockets being configured to receive each connector of the plurality of connectors, and wherein each socket of the plurality of sockets is separated from an adjacent socket of the plurality of sockets by a portion of the connector plate and is configured to electrically connect to a corresponding socket in the at least one receiving unit.

Optionally, the control unit is further configured to determine at least one of authentication data or data indicative of a production date of the plurality of connectors or the electrodes by receiving, via at least one connector of the plurality of connectors, data indicative of the at least one of authentication data or data indicative of the production dates of the plurality of connectors or the electrodes.

Optionally, the control unit is configured to generate data indicative of, or associated with, a three-dimensional image. The three-dimensional image may comprise a plurality of pixel positions and wherein at least one of the plurality of pixel positions is associated, in a memory, with at least one of the electrodes. Optionally, the control unit is configured to receive data indicative of a user input selecting at least one of the plurality of pixel positions of the three-dimensional image and is configured to identify at least one electrode associated with the selected at least one of the plurality of pixel positions based on the user input. Optionally, the control unit is further configured to determine data associated with the identified at least one electrode by using the unique identification code associated with the at least one electrode.

Optionally, the control unit is configured to automatically populate at least one graphical user interface with data indicative representative of each of the electrodes based on the unique identification codes. Optionally, the control unit is configured to automatically update data displayed in the at least one graphical user interface with updated data indicative representative of each of the electrodes based on the unique identification codes after one or more of the electrodes is moved or disconnected and reconnected to the at least one receiving unit.

Optionally, the control unit is configured to receive data indicative of a user selection of a trace displayed on a graphical user interface, wherein, upon receiving data indicative of the user selection of the trace, the control unit is configured to trigger a visual indicator positioned in physical proximity to or association with one of the electrodes that acquired data associated with said trace. Optionally, the visual indicator is at least one of a light positioned on the one of the electrodes, a light positioned on a connector of the plurality of connectors in data communication with the one of the electrodes, or a light positioned on a lead attached to the one of the electrodes.

Optionally, the electrodes are configured in groups of 4, 5, 6, 7, 8, 9, 10, 11, 12, 13, 14, 15 or 16 electrodes.

Optionally, the system is configured to perform at least one of an electroencephalography, electrocardiogram, electromyography, polysomnography, or intraoperative neural monitoring procedure.

The unique identification code associated with each said electrode group lead may be stored in association with each electrode group lead, wherein the unique identification code is configured as any one of a crimp, an adhesive label or an embedded code on each electrode group lead.

Optionally, each connector of the plurality of connectors further comprises a value wherein the value is representative of a number of permissible uses of the connector of the plurality of connectors. The value may be indicative of a maximum number of sterilization cycles of the connector of the plurality of connectors wherein the maximum number of sterilization cycles is equal to, or less than, 20.

Optionally, the control unit is configured to access a value associated with each connector of the plurality of connectors, wherein the value is indicative of a maximum number of sterilization cycles of the connector of the plurality of connectors wherein the maximum number of sterilization cycles is equal to, or less than, 20.

The present specification also discloses a method for neuromonitoring or neurodiagnostics comprising: acquiring a plurality of electrode groups, wherein each group of the plurality of electrode groups comprises electrodes, wherein each of the electrodes in each group has a similar monitoring functionality type and/or a similar deployment location and wherein each of the plurality of electrode groups has at least one electrode group lead; coupling each of the at least one electrode group leads to a connector of a plurality of connectors, wherein each of the at least one electrode group leads and/or each connector of the plurality of connectors is electronically associated with a unique identification code; coupling each connector of the plurality of connectors to a socket in a control unit; using the control unit, determining at least one of the unique identification code of each connector of the plurality of connectors or the unique identification code of each of the at least one electrode group leads; and using the control unit, associating each electrode in the plurality of electrode groups with a corresponding input channel in the control unit based on at least one of the unique identification code of each connector or the unique identification code of each of the at least one electrode group leads, such that each electrode in the plurality of electrode groups is uniquely associated with only one input channel in the control unit.

The unique identification code may be in a 128 bit GUID format.

Optionally, determining at least one of the unique identification code of each connector of the plurality of connectors or the unique identification code of each of the at least one electrode group leads is executed in the control unit by receiving, via each connector of the plurality of connectors, data indicative of at least one of the unique identification code of each connector of the plurality of connectors or the unique identification code of each of the at least one electrode group leads.

Optionally, the method further comprises receiving, in the control unit and via each connector of the plurality of connectors through a direct pin-to-pin electrical pass through, data indicative of at least one of the unique identification code of each connector of the plurality of connectors or the unique identification code of each of the at least one electrode group leads.

Optionally, the method further comprises receiving, in the control unit and via each connector of the plurality of connectors through a direct pin-to-pin electrical pass through, data indicative of at least one of a production date of the plurality of connectors, a production date of the electrodes, or authentication information.

Each connector may comprise a designated output pin wherein the designated output pin is configured to transfer information related to the unique identification code to the control unit.

Data indicative of the unique identification code may be stored in a memory associated with the designated output pin.

Data indicative of the unique identification code may comprise a bar code or a radio frequency code (RFID).

Data indicative of the unique identification code may be stored using at least one pin configured as at least one dip switch comprising at least one resistor.

Each connector of the plurality of connectors may be configured to be inserted in the control unit in at least two different orientations.

Optionally, each connector of the plurality of connectors comprises at least two designated output pins, each of which being configured to convey data indicative of the unique identification code and an orientation of a connector of the plurality of connectors. Optionally, the at least two designated output pins are configured to be at different polarities or at different voltage levels to indicate the orientation of the connector of the plurality of connectors. Optionally, a physical position of the at least two designated output pins is different in each of the at least two different orientations.

Optionally, the method further comprises inserting each connector of the plurality of connectors into an opening in a rigid connector plate and concurrently inserting each connector of the plurality of connectors into corresponding sockets in the control unit by pushing the connector plate toward the control unit. Optionally, the method further comprises partially positioning each connector of the plurality of connectors in each opening such that a first end of each connector extends outward from a first surface of the connector plate and a second end, opposing the first end, of each connector extends outward from a second surface of the connector plate, wherein the second surface opposes the first surface.

Optionally, the method further comprises inserting each connector of the plurality of connectors into a corresponding socket in a rigid connector plate, wherein each corresponding socket has a first end configured to connect to a connector of the plurality of connectors and a second end configured to connect to a corresponding socket in the control unit, and concurrently placing each connector of the plurality of connectors into electrical communication with the control unit by pushing the connector plate toward the control unit such that the second end of each socket is placed into electrical communication with each corresponding socket in the control unit.

Optionally, the method further comprises receiving, into the control unit and via at least one connector of the plurality of connectors, data indicative of at least one of authentication data or data indicative of the production dates of the plurality of connectors or the electrodes and determining, using the control unit, at least one of authentication data or data indicative of a production date of the plurality of connectors or the electrodes.

Optionally, the method further comprises, using the control unit, generating data indicative of, or associated with, a three-dimensional image. The three-dimensional image may comprise a plurality of pixel positions wherein at least one of the plurality of pixel positions is associated, in a memory, with at least one of the electrodes. Optionally, the method further comprises receiving, in the control unit, data indicative of a user input selecting at least one of the plurality of pixel positions of the three-dimensional image and, using the control unit, identifying at least one electrode associated with the selected at least one of the plurality of pixel positions based on the user input. Optionally, the method further comprises determining trace data associated with the identified at least one electrode by using the unique identification code associated with the at least one electrode.

Optionally, the method further comprises automatically populating at least one graphical user interface with data indicative representative of each of the electrodes based on the unique identification codes. Optionally, the method further comprises automatically updating data displayed in the at least one graphical user interface with updated data indicative representative of each of the electrodes based on the unique identification codes after one or more of the electrodes is moved or disconnected and reconnected to the control unit.

Optionally, the method further comprises receiving, in the control unit, data indicative of a user selection of a trace displayed on a graphical user interface, wherein, upon receiving data indicative of the user selection of the trace, triggering a visual indicator positioned in physical proximity to or association with one of the electrodes that acquired data associated with said trace. The visual indicator may be at least one of a light positioned on the one of the electrodes, a light positioned on a connector of the plurality of connectors in data communication with the one of the electrodes, or a light positioned on a lead attached to the one of the electrodes.

Optionally, the method further comprises coupling each of the electrode group leads to each of the connectors in a predefined order.

Optionally, the electrodes are configured in groups of 4, 5, 6, 7, 8, 9, 10, 11, 12, 13, 14, 15 or 16 electrodes.

Optionally, the method further comprises performing at least one of an electroencephalography, electrocardiogram, electromyography, polysomnography, or intraoperative neural monitoring procedure.

Optionally, the method further comprises storing the unique identification code, which is electronically associated with each of the electrode group leads, in physical association with each electrode group lead, wherein the storing of the unique identification code in physical association is achieved using any one of a crimp, an adhesive label or an embedded code on each electrode group lead.

Each connector of the plurality of connectors may further comprise a value and wherein the value is representative of a number of permissible uses of the connector of the plurality of connectors. The value may be indicative of a maximum number of sterilization cycles of the connector of the plurality of connectors wherein the maximum number of sterilization cycles is equal to, or less than, 20.

Optionally, the method further comprises, using the control unit, accessing a value associated with each connector of the plurality of connectors and limiting a number of times each connector of the plurality of connectors is used based on the value. The value may be indicative of a maximum number of sterilization cycles of the connector of the plurality of connectors. The maximum number of sterilization cycles may be equal to, or less than, 20.

The present specification also discloses a system for neuromonitoring and neurodiagnostics comprising: a plurality of electrode groups wherein each group comprises electrodes, each of said electrodes in each group having at least one of a similar monitoring functionality type or a similar deployment location and having at least one electrode group lead; a plurality of connectors, wherein each electrode group lead of said plurality of electrode groups is coupled to at least one connector of said plurality of connectors, and wherein either each electrode group lead of said plurality of electrode groups or each connector of said plurality of connectors carries an associated unique identification code; and, a control unit comprising at least one receiving unit configured for receiving said plurality of connectors, establishing an identity of each connector of said plurality of connectors by identifying each unique identification code associated with each connector of said plurality of connectors or establishing an identity of each electrode group lead of said plurality of electrode group by identifying each unique identification code associated with each electrode group lead of said plurality of electrode groups, and configuring the system to associate each electrode with a corresponding input channel in the control unit based on said unique identification code.

Optionally, said unique identification code is in a 128 bit GUID format.

Optionally, said at least one receiving unit comprises a plurality of input sockets configured to receive one or more connectors of said plurality of connectors. Optionally, said one or more connectors are configured to be coupled to any of the plurality of input sockets of said at least one receiving unit.

Optionally, said connector has a designated output pin which is configured to transmit information related to the unique identification code to said control unit. Optionally, the information related to the unique identification code is formatted as a bar code or a radio frequency code (RFID). Optionally, the information related to the identification code is stored using multiple pins that are configured as dip switches comprising resistors.

Optionally, each of said plurality of connectors is configured to be inserted in said receiving unit using at least two different orientations. Optionally, each of said plurality of connectors has two designated output pins which are configured to transmit information related to the unique identification code and an orientation of the connector to said control unit. Optionally, the two designated output pins are maintained at different polarities or voltage levels to indicate the orientation of the connector as inserted in a receiving unit. Optionally, a physical position of said two designated output pins is different in each of two orientations.

Optionally, said electrode group leads are coupled to inputs of the at least one connector in a predefined order.

Optionally, said electrodes are configured in groups of 4, 6, 8, 10, 12 or 16 electrodes.

Optionally, said system is configured to perform an EEG, PSG, EMG, or neuromonitoring procedure.

Optionally, said system is configured to perform an EKG procedure.

Optionally, the unique identification code associated with each said electrode group lead is positioned on each electrode group lead, and wherein the unique identification code is configured as any one of a crimp, an adhesive label or an embedded code on each electrode group lead.

The present specification also discloses a medical system for monitoring of patient data comprising: a plurality of electrode groups configured to be attached to a body of a patient wherein each electrode group in said plurality of electrode groups comprises electrodes of a similar type having at least one of a similar monitoring functionality type or a similar deployment location and having at least one electrode group lead; a plurality of connectors wherein each connector includes a unique identification code and wherein each electrode group lead of said plurality of electrode groups is coupled to at least one connector of said plurality of connectors; and, a control unit comprising at least one receiving unit configured for receiving said plurality of connectors, establishing an identity of each of said plurality of connectors by identifying each unique identification code associated with each of said plurality of connectors, and configuring the system to relate each electrode with its corresponding input channel in the control unit based on said identification code, wherein relate is defined as placing the electrode in electrical communication with the corresponding input channel.

Optionally, said medical system is configured to be used for neuromonitoring and neurodiagnostics applications. Optionally, the neuromonitoring and neurodiagnostics applications include EEG, EMG, IONM, and PSG.

Optionally, said medical system is configured to be used for an EKG procedure.

Optionally, said unique identification code includes a counter to limit the number of uses of the associated connector.

Optionally, said counter is indicative of a maximum number of sterilization cycles of the associated connector, and wherein the maximum number is in a range of 5 to 20 sterilization cycles.

The present specification also discloses a medical system for monitoring of patient data comprising: a plurality of electrode groups configured to be attached to a body of a patient wherein each electrode group in said plurality of electrode groups comprises electrodes of a similar type having at least one of a similar monitoring functionality type or a similar deployment location and having at least one electrode group lead, wherein each electrode group lead includes a unique identification code; a plurality of connectors, wherein each electrode group lead of said plurality of electrode groups is coupled to at least one connector of said plurality of connectors; and, a control unit comprising at least one receiving unit configured for receiving said plurality of connectors, establishing an identity of each of said electrode groups identifying each unique identification code associated with each of said electrode group leads, and configuring the system to relate each electrode with its corresponding input channel in the control unit based on said identification code, wherein relate is defined as placing the electrode in electrical communication with the corresponding input channel.

The present specification also discloses a system for neuromonitoring and neurodiagnostics comprising: a plurality of electrode groups wherein each group comprises electrodes, each of said electrodes in each group having at least one of a similar monitoring functionality type and a similar deployment location; a plurality of connectors wherein each connector comprises an electronically accessible memory and wherein a unique identification code is stored in each electronically accessible memory and wherein each electrode group of said plurality of electrode groups is coupled to at least one connector of said plurality of connectors; and, a control unit comprising at least one receiving unit configured for receiving said plurality of connectors, establishing an identity of each connector of said plurality of connectors by identifying each unique identification code associated with each connector of said plurality of connectors, and configuring the system to associate each electrode with a corresponding input channel in the control unit based on said unique identification code.

Optionally, said unique identification code is in a Global Unique Identifier (GUID) format, such as 128 bit.

Optionally, said at least one receiving unit comprises a plurality of input sockets configured to receive one or more connectors of said plurality of connectors.

Optionally, said one or more connectors are configured to be coupled to any of the plurality of input sockets of said at least one receiving unit.

Optionally, said connector has a designated communication method which is configured to transmit information related to the unique identification code to said control unit.

Optionally, the information related to the unique identification code is formatted as a bar code or a radio frequency code (RFID).

Optionally, the information related to the unique identification code is stored in the electrode or electrode group and passed through the receiving unit to the control unit.

Optionally, the information related to the identification code is stored using multiple pins that are configured as dip switches comprising resistors.

Optionally, each of said plurality of connectors is configured to be inserted in said receiving unit using at least two different orientations.

Optionally, each of said plurality of connectors has two designated output pins which are configured to transmit information related to the unique identification code and an orientation of the connector to said control unit.

Optionally, the two designated output pins are maintained at different polarities or voltage levels to indicate the orientation of the connector as inserted in a receiving unit.

Optionally, a physical position of said two designated output pins is different in each of two orientations.

Optionally, electrodes included in any one electrode group are coupled to inputs of the connector in a predefined order.

Optionally, said electrodes are configured in groups of 4, 6, 8, 10, 12 or 16 electrodes.

Optionally, said system is configured to perform an EEG or EMG procedure. Optionally, said system is configured to perform a PSG or neuromonitoring procedure.

The present specification also discloses a method for neuromonitoring and neurodiagnostics comprising: providing a plurality of electrodes for deploying on different portions of a human body; arranging said electrodes in a plurality of electrode groups wherein each group comprises electrodes having at least one of a similar monitoring functionality type and a similar deployment location; coupling the electrodes of each one of said plurality of electrode groups with one connector of a plurality of connectors, wherein each connector comprises a unique identification code stored in an electronically accessible memory in said connector; coupling each connector of said plurality of connectors with at least one receiving unit in communication with a system control unit; establishing the identity of each connector of said plurality of connectors from its unique identification code, wherein said receiving unit is configured to establish said identity by identifying each unique identification code associated with each connector of said plurality of connectors; and, configuring the system to associate each electrode with its corresponding input channel in said control unit based on said unique identification code.

Optionally, said unique identification code is in a GUID format, such as 128 bit.

Optionally, said at least one receiving unit comprises input sockets in which one or more said connectors can be inserted.

Optionally, said connectors are connectors are configured to be coupled to any of the inputs of said at least one receiving unit.

Optionally, said connector has a designated communication method which is configured to transmit information related to the unique identification code to said control unit.

Optionally, the information related to identification code is communicated through a bar code or a radio frequency code (RFID).

Optionally, the information related to identification code is communicated from the electrode or electrode group through the receiving unit to the control unit.

Optionally, each of said plurality of connectors is configured to be inserted in said at least one receiving unit using at least two different orientations, wherein said at least two different orientations comprise at least a first orientation and at least a second orientation, wherein said second orientation is rotated 180 degrees about a horizontal axis with respect to said at least first orientation.

Optionally, each of said plurality of connectors has two designated output pins which are configured to transmit information related to the identification code and an orientation of the connector to said control unit.

Optionally, the two designated output pins are maintained at different polarities or voltage levels to indicate the orientation of the connector as inserted in a receiving unit.

Optionally, a physical position of said two designated output pins is different in each of said at least two orientations.

Optionally, electrodes included in any one of said group of electrodes are coupled to inputs of the connector in a predefined order.

Optionally, said electrodes are combined in groups of 4, 6, 8, 10, 12 or 16 electrodes.

Optionally, said method may be used to perform an EEG or EMG procedure. Optionally, said method may be used to perform a PSG or neuromonitoring procedure.

The present specification also discloses a medical system for monitoring of patient data comprising: a plurality of electrode groups configured to be attached to a body of a patient wherein each electrode group in said plurality of electrode groups comprises electrodes of a similar type having at least one of a similar monitoring functionality type and a similar deployment location; a plurality of connectors wherein each connector comprises an electronically accessible memory and wherein a unique identification code is stored in each electronically accessible memory and wherein each electrode group of said plurality of electrode groups is coupled to at least one connector of said plurality of connectors; and, a control unit comprising at least one receiving unit configured for receiving said plurality of connectors, establishing an identity of each of said plurality of connectors by identifying each unique identification code associated with each of said plurality of connectors, and configuring the system to relate each electrode with its corresponding input channel in the control unit based on said identification code, wherein relate is defined as placing the electrode in electrical communication with the corresponding input channel.

Optionally, said medical system is configured to be used for neuromonitoring and neurodiagnostics applications.

Optionally, said medical system is configured to be used for an EKG procedure.

The aforementioned and other embodiments of the present specification shall be described in greater depth in the drawings and detailed description provided below.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout.

FIG. 4A shows an illustration of connectors of different sizes in accordance with various embodiments of the present specification;

DETAILED DESCRIPTION

Figure 1:
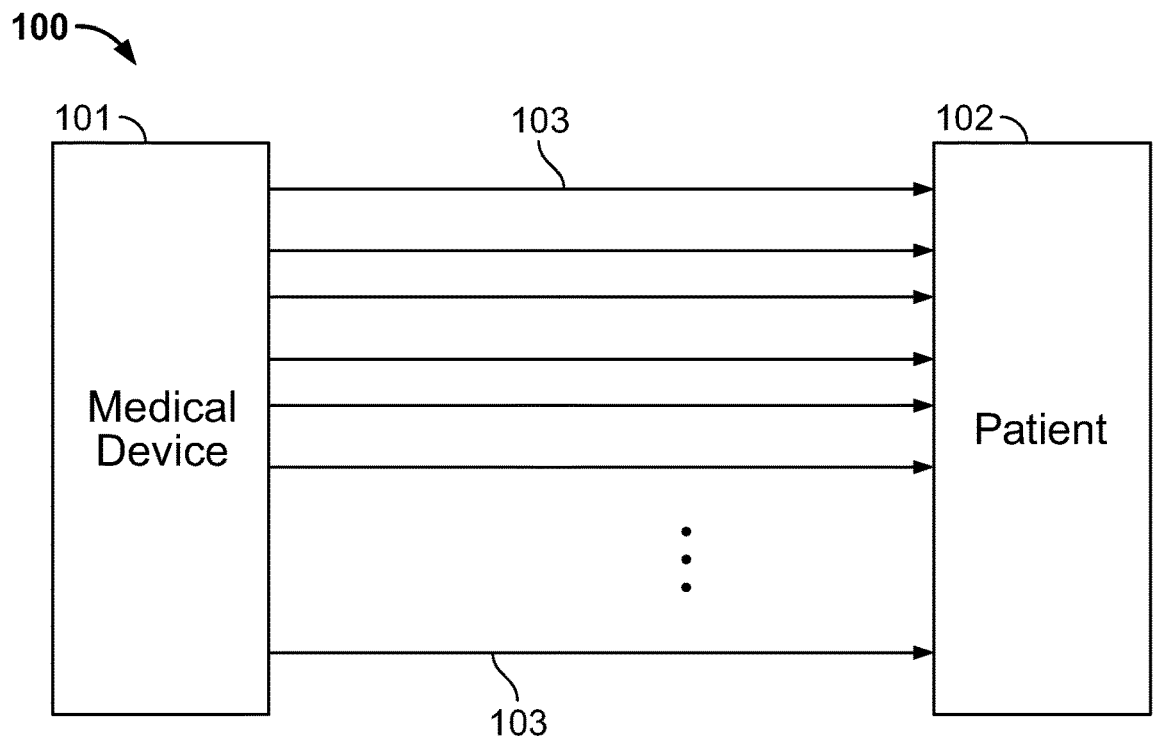
FIG. 1 shows a block diagram of a conventional medical system comprising a large number of electrodes deployed on a patient body.

The system, devices, and methods described below disclose a novel electrode management solution for neuromonitoring and neurodiagnostics applications such as electroencephalography (EEG) procedures. Systems and methods are disclosed which provide a highly reliable and convenient method for electrode management in such applications. In embodiments of the disclosed system, the physician is not required to manually match each electrode lead with its corresponding input channel on the system control unit, significantly reducing the set up time and reducing errors. The electrodes are not directly connected with the input channels in the control unit or the amplifier of the neuromonitoring and neurodiagnostics system. Rather, the control unit is coupled to electrodes or groups of electrodes with the help of unique connectors and corresponding receiving sockets which enable automatic detection of the electrodes, including their type and deployment location. Once the electrodes are identified, the control unit reconfigures the system to automatically correlate, associate, assign, or 'map', each electrode with its corresponding input channel in the control unit, wherein correlate, associate, assign, relate, or map is defined as placing a specific electrode in electrical communication with the corresponding specific input channel in the control unit. The connectors and receiving sockets ensure the control unit will recognize each electrode properly and process information received from each electrode correctly with respect to the electrodes placement position on the patient's body, regardless of where the connector is inserted into the receiving socket.

In embodiments, the electrodes are arranged into a plurality of groups such that the electrodes of similar type, based on their similar monitoring functionality and similar deployment location on a human body, are included in the same group. Multiple electrodes become easier to manage when they are grouped for connection to the connectors (or mass termination blocks) of the present specification. Thus, grouping of multiple electrodes facilitates management. For purposes of the present specification, the term "similar monitoring functionality" shall mean electrodes that are used for similar neuromonitoring and neurodiagnostics modalities. For example, electrodes used for studies including, but not limited to, electroencephalography (EEG), electromyography (EMG), polysomnography (PSG), intraoperative neural monitoring (IONM) and evoked potentials are gathered into groups of similar monitoring functionality. Accordingly, all electrodes being used for an EEG constitute electrodes having a similar monitoring functionality and are expressly differentiated from (and therefore do not have similar monitoring functionality as) those electrodes being used for other modalities, such as an EMG. For purposes of the present specification, the term "similar deployment location" shall mean electrodes that are positioned together in a specific area on a patient's head, scalp, or brain. For example, electrodes configured to be placed on a front, back, left side, or right side of a patient's scalp or brain would be gathered into groups of similar deployment location based on each area. Accordingly, all electrodes being deployed in front side of a patient's scalp or brain constitute electrodes having a similar deployment location and are expressly differentiated from (and therefore do not have a similar deployment location as) those electrodes being deployed on the back side, left side, or right side of the patient's scalp, each of those being different deployment locations.

Subsequently, each group of electrodes is mapped to a separate connector in a pre-defined order and all such connectors are coupled with a receiving socket on the system control unit. When a group of electrodes are mapped to a connector, the exact position and type of each electrode in that group is standardized, as the electrodes are coupled to a connecter in a pre-defined order, and the connector is assigned a unique identification code or ID. As an alternate embodiment, the unique identification code may be transmitted from the electrode or group of electrodes through the connectors to the receiving sockets in the control unit. The connectors and the receiving sockets have an identity (ID) read capability such that when any connector is inserted in the receiving socket, the receiving socket can identify the connector from its unique identification code or ID and based on the identity of the connector, the specific location and type of all the electrodes mapped to this connector are established. The ID information is carried explicitly by the connector (or the electrode or group of electrodes and transmitted by the connector), and not implicitly by the receptacle. The ID information is stored in electronically accessible memory on the connector, electrode, or group of electrodes. In various embodiments, the memory is any one or combination of non-volatile memory, such as read-only memory (ROM), programmable read-only memory (PROM), erasable programmable read-only memory (EPROM), and electronically erasable programmable read-only memory (EEPROM), and volatile memory, such as dynamic random-access memory (DRAM) and static random-access memory (SRAM). Alternatively, the ID information may be stored in RFID, barcode, or other non-volatile format. The electrodes of a group and the connector are never separated, and if the connector is reinserted elsewhere on an array of available inputs, the system will remap the inputs to the correct channels. Therefore, the system allows for the unplugging of a connector from a physical port and subsequent relocation of the connector to a different physical port, even a physical port on a different amplifier, while retaining the logical mapping of each electrode. Automatic mapping of electrodes as connectors are removed and placed in a different location ensures data associated with each electrode is correctly reported. The ID information is for all electrodes in a group, which, in some embodiments, is at least 16 at a time, compared to one electrode at a time which is encountered in current systems. The information needed to determine where the electrode is attached is a function of at least one or more of the connector, electrode, or electrode group (using its unique ID) and either a pre-defined setup (for example, in the case of a 10/20 system headcap) or a setup specified on a per connector basis by the user to a computer system.

In embodiments, when a connector is coupled with a receiving socket, the medical system requests for the information on the electrodes coupled to each input of that connector. The user subsequently provides information on the various electrodes coupled to the specific inputs of the connector. In an embodiment, the user manually inserts this information (or selects the data from a list of available options) through an electronic keyboard or keypad coupled with the medical system. Once the user provides this information, the exact position and type of each electrode in a group coupled with a specific connector is standardized. In some alternate embodiments, the standardized information related to exact order in which electrodes are coupled to each connector is provided to the medical system before inserting the connectors in the receiving socket. In another alternate embodiment, information about the electrode or electrode group, such as a unique ID, number of electrodes, size, or shape is contained in the ID stream coming directly from the electrode or electrode group.

The receiving socket comprises a bank of input points and is configured such that various connectors having unique IDs and representing separate groups of electrodes can be inserted in any of the inputs on the receiving socket. Once the receiving socket establishes an electrical connection with a connector, it can read the unique ID of the connector to establish its identity. On establishing the identity of the connector, the system is able to recognize the type and specific location of various electrodes mapped to the connector.

Using the concept of connectors with unique ID as disclosed herein, the position of the electrodes in a specific group is standardized with respect to the connector. The electrodes from the same group are coupled to inputs of the connector in a pre-defined sequence and the system reading the unique ID of the connector assigns the correct meaning (electrode type and location) to each input. In embodiments, the system includes a pre-defined list of available electrodes (catalog items that are available from manufacturers) and the medical care provider needs to ensure that the correct electrode(s) corresponding to a single connecter are mapped to each unique ID of the connector. For example, if an electrode has multiple leads, such as four leads with 16 electrical contacts each (which is the case with a 64-lead grid electrode in an 8×8 array), then the care provider needs to ensure that each of the four leads (1-4) for the 8×8 grid electrode are properly mapped to the correct connector. Thus, a total of four logical mappings reside in the software application, versus the need to plug 64 color coded connectors into the correct amplifier channel number. Once identified, the electrode groups can be removed and reinserted in any available slot in the system, for example, to other slots within the same amplifier, to another amplifier, or to a new amplifier (replacing an amplifier altogether), without error. The system will note the new connection and assign the correct meaning to the input. Handling electrode leads in small groups makes the entire set up process less cumbersome in case of high density electrode applications, such as EEG procedures involving a large number of electrodes, for example greater than 64 or even more than 500. In conventional systems, if the electrical connectors corresponding to electrodes are removed and reinserted into receptacles located within the medical device, each electrical connector has to be reinserted into exactly the same receptacle or the electrode body site to channel display will be incorrect. However, in the above disclosed system, the user can remove the various connectors from the medical device and can reinsert these connectors in any of the input points in the receiving sockets.

In some embodiments, the systems and methods of the present specification also provide reverse identification of electrodes and/or connectors from a software application. Once standardized information relating to an electrode or connector is established as described in the present specification (for example, via a unique ID of a connector), a user may select a graphical representation of an electrode or connector (for example, a signal trace displayed on a user interface) to identify the specific physical electrode or connector associated therewith. In some embodiments, electrodes (and/or leads of the electrodes) and connectors of the present specification include lights which illuminate in response to specific actions by a user. In one embodiment, a user may click on a trace displayed on a graphical user interface (GUI) of the system which triggers a connector visual indicator, such as a light (positioned proximate to or on) a connector to illuminate, providing visual identification of the corresponding connector to the user. In another embodiment, a user may click on a trace displayed on GUI of the system which triggers an electrode visual indicator, such as a light (positioned proximate to or on) an electrode (for example, an electrode positioned on a patient's scalp) to illuminate, providing visual identification of the corresponding electrode to the user. In yet another embodiment, a user may click on a trace displayed on GUI of the system which triggers a lead visual indicator, such as a light (positioned proximate to or on) a lead attached to an electrode (for example, a lead attached to an electrode positioned in a patient's brain) to illuminate, providing visual identification of where the corresponding electrode enters a patient's skull.

An exemplary beneficial use of the connector systems of the present specification is with an MRI procedure. During an MRI, the monitoring system amplifier inputs need to be disconnected from the amplifier itself as the amplifier is not allowed into the intense magnetic fields generated by the MRI machine. Disconnecting and reconnecting 200 leads for such a procedure is time consuming and error prone. Such a laborious process can preclude the use of an MRI procedure, even if it is the preferred imaging technique. If an amplifier fails, the leads would need to be moved. In a set of 200 non-identified individual leads, the process is not only error prone, but each channel would have to be remapped manually, and in some systems, the channels have to be used consecutively, so the 'abandoned' channels continue to be displayed. In the identified connector systems of the present specification, there is less chance for error in reconnecting the leads and the process is much quicker.

A "computing device" refers to at least one of a cellular phone, PDA, smart phone, tablet computing device, patient monitor, custom kiosk, or other computing device capable of executing programmatic instructions. It should further be appreciated that each device and monitoring system may have wireless and wired receivers and transmitters capable of sending and transmitting data. Each "computing device" may be coupled to at least one display, which displays information about the patient parameters and the functioning of the system, by means of a GUI. The GUI also presents various menus that allow users to configure settings according to their requirements. The system further comprises at least one processor to control the operation of the entire system and its components. It should further be appreciated that the at least one processor is capable of processing programmatic instructions, has a memory capable of storing programmatic instructions, and employs software comprised of a plurality of programmatic instructions for performing the processes described herein. In one embodiment, the at least one processor is a computing device capable of receiving, executing, and transmitting a plurality of programmatic instructions stored on a volatile or non-volatile computer readable medium. In addition, the software comprised of a plurality of programmatic instructions for performing the processes described herein may be implemented by a computer processor capable of processing programmatic instructions and a memory capable of storing programmatic instructions.

"Electrode" refers to a conductor used to establish electrical contact with a nonmetallic part of a circuit. EEG electrodes are small metal discs usually made of stainless steel, tin, gold or silver covered with a silver chloride coating. They are typically placed on the scalp on predetermined locations.

A "subdural electrode grid" refers to a thin sheet of material with multiple small (roughly a couple mm in size) recording electrodes implanted within it. These are placed directly on the surface of the brain and have the advantage of recording the EEG without the interference of the skin, fat tissue, muscle, and bone that may limit scalp EEG. Shapes and sizes of these sheets are chosen to best conform to the surface of the brain and the area of interest.

A "depth electrode" refers to small wires that are implanted within the brain itself. Each wire has electrodes which surround it. These electrodes are able to record brain activity along the entire length of the implanted wire. They have the advantage of recording activity from structures deeper in the brain. They can be implanted through small skin pokes.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise" "include" and "have", and forms thereof, are not necessarily limited to members in a list with which the words may be associated. It should be noted herein that any feature or component described in association with a specific embodiment may be used and implemented with any other embodiment unless clearly indicated otherwise.

FIG. 1 show a block diagram of a conventional medical system 100 comprising a large number of electrodes deployed on a patient 102 body. The medical device 101 represents any conventional neuromonitoring and neurodiagnostics medical system which comprises a large number of electrodes, such as an EEG (electroencephalography) system, which is used for monitoring the neurological state of a patient for diagnosis and preventive treatment of certain diseases and for monitoring patients during anesthesia, among other procedures. As shown in FIG. 1, the medical device 101 is coupled to the patient 102 through a plurality of electrical leads 103 such that each of the leads 103 is coupled to an electrode (not shown) positioned at an appropriate location on the body of the patient. In applications that require a large number of electrodes to be coupled to the human body, the setup, placement and management of electrodes is a cumbersome process. As each electrode is positioned at a different location to capture the electrical activity in its vicinity, the input recorded from each electrode has to be processed independently. Therefore, the system is required to recognize the identity of each of the electrical leads 103 and accordingly process the input received from it. After positioning any electrode at its required location on the body of the patient 102, the user is required to correctly insert the electrode lead 103 corresponding to each electrode in a specific input channel configured for that electrode in the medical device 101. In case the number of electrodes is small, for example, less than ten or fifteen, it is possible for the user to identify and connect electrodes with the correct input channels. However, as the number of electrodes increases, this process become very difficult and is prone to error. Further, even if the electrodes are coupled to the correct input slots in the medical device 101, it is practically very difficult and time consuming to recheck and verify the integrity of each connection before every procedure. Usually, in such high density configurations, the set up process is so time consuming that in some circumstances, for example during a surgical procedure, the user completely or partially skips the step of checking each connection for integrity until after the surgery is finished, which increases the possibility of error in the procedure.

Figure 2:
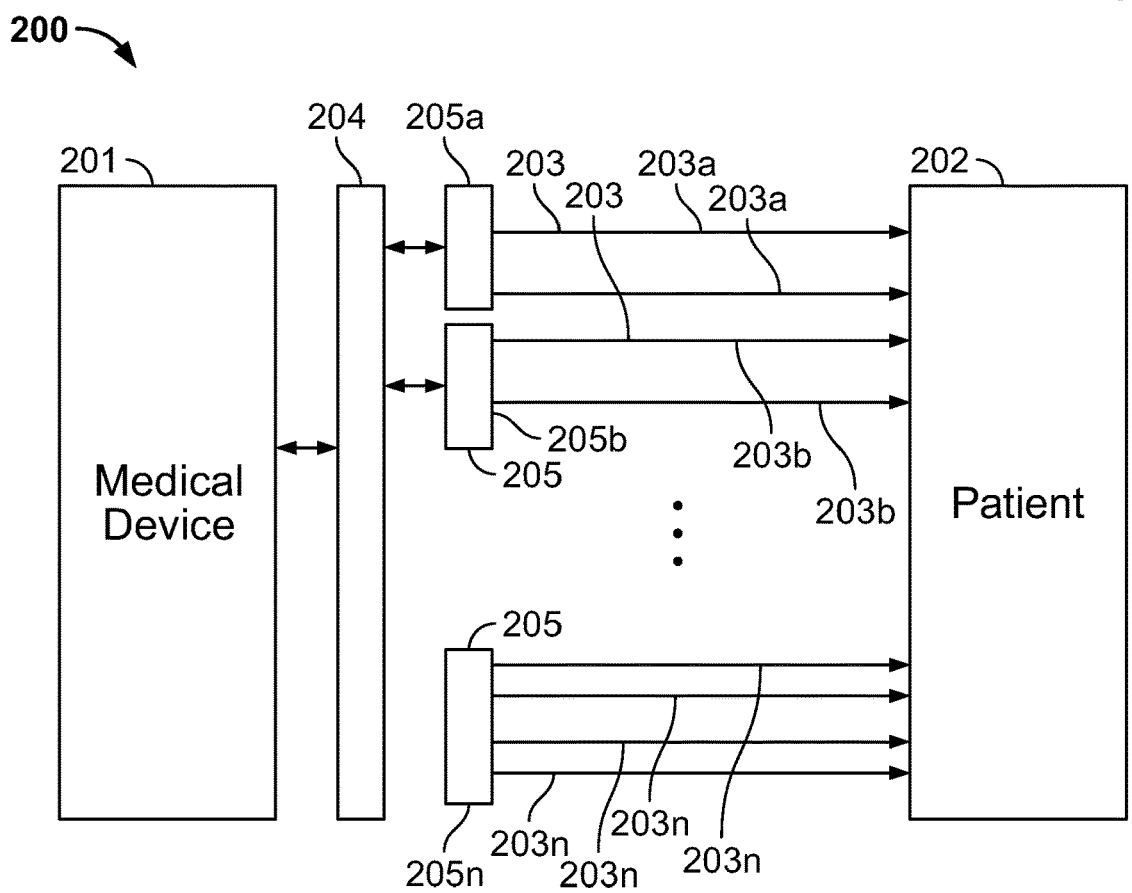
FIG. 2 shows a block diagram of an illustrative medical system comprising a large number of electrodes deployed on the body of a patient as disclosed in accordance with an embodiment of the present specification.

FIG. 2 shows a block diagram of an illustrative medical system 200 comprising a large number of electrodes deployed on the body of a patient 202 as disclosed in an embodiment. The medical device 201 comprises a number of electrodes (not shown) coupled to the body of the patient 202 through a plurality of electrical leads 203. In neuromonitoring and neurodiagnostics medical procedures such as EEG, the electrodes come in groups such that the electrodes in a specific group have similarities in terms of their input signal and positioning. In the systems and methods described herein, the electrodes and the corresponding electrical leads 203 are also arranged in a plurality of groups such as 203a, 203b, . . . , 203n such that each of these groups comprises electrodes of similar type and location and is configured independently. In the disclosed arrangement, instead of directly connecting the medical device 201 with the deployed electrodes, the electrodes are arranged in groups and each group is coupled to the medical device 201 through a connector 205 having a unique ID. Each of the groups of electrical leads 203a, 203b, . . . , 203n (representing electrodes of similar type and location) is coupled to a corresponding connector 205a, 205b, . . . , 205n such that the group of electrical leads 203a is coupled to the connector 205a, the group of electrical leads 203b is coupled to the connector 205b, and similarly the group of electrical leads 203n is coupled to the connector 205n. The various connectors 205a, 205b . . . , 205n are connected with a receiving socket 204 which is coupled to the medical device 201. The receiving socket 204 comprises a bank of inputs and is configured to receive the connectors 205a, 205b, . . . , 205n in any of these inputs. Each of the connectors 205a, 205b, . . . , 205n has an independent identity and the receiving socket 204 is configured to establish the identity of any such connector when the same is connected with it. By establishing the identity of any connector 205, the system 200 is able to identify the various electrodes, including their type and location, coupled to each connector 205. All the electrodes coupled to a single connector 205 belong to the same group and are hence interchangeable in terms of their signal conditioning requirements. The anatomic positions of the patient connected electrodes coupled to the corresponding electrical leads 203 are always in the same defined input sequence on connector 205. Further, as the receiving socket 204 is configured to identify any connector 205 from its unique ID and, therefore, the group of electrodes coupled to that connector 205, the connectors can be plugged into any of the inputs in receiving socket 204.

In an embodiment, the connectors 205a, 205b, . . . , 205n comprise a designated pre-defined identification output point/pin such that, when any connector is plugged into the receiving socket 204, the receiving socket 204 reads the information received from the output pin to establish the identity of the connector 205. Once the identity of a connector 205 is established, the system 200 recognizes the set of electrodes mapped with that connector 205 and reconfigures itself to automatically correlate, associate or map each electrode with its corresponding input channel.

Using the concept of handling electrodes in independent groups as described above, instead of manually mapping each electrode with its corresponding input channel in the medical device 201, the user only needs to ensure that the electrodes belonging to the same group are coupled to the same connector in the same order. This occurs by default when the inputs are part of a mechanically defined grid or strip. Subsequently, the user can insert multiple such connectors in a receiving socket in any of its inputs. The disclosed method significantly reduces the set up time required before starting any medical procedure as the conventional process of manually mapping electrodes with input channels is very tedious and time consuming. Disclosed systems and methods also reduce the risk of error by obviating the human involvement in mapping of electrodes with corresponding input channels.

The number of electrodes coupled to any of the connectors 205 can vary and is dependent on the actual medical requirement. Usually, the electrodes which are deployed in the similar location and receive similar input signal can only be grouped and coupled to a single connector. In medical procedures such as an EEG, the electrodes come in groups of 4, 5, 6, 8, 10 and 16 electrodes, wherein each such group is targeted towards a specific part of the brain. In such cases, multiple different sized connectors are deployed which are capable of supporting the above mentioned groups of electrodes.

Figure 3A:
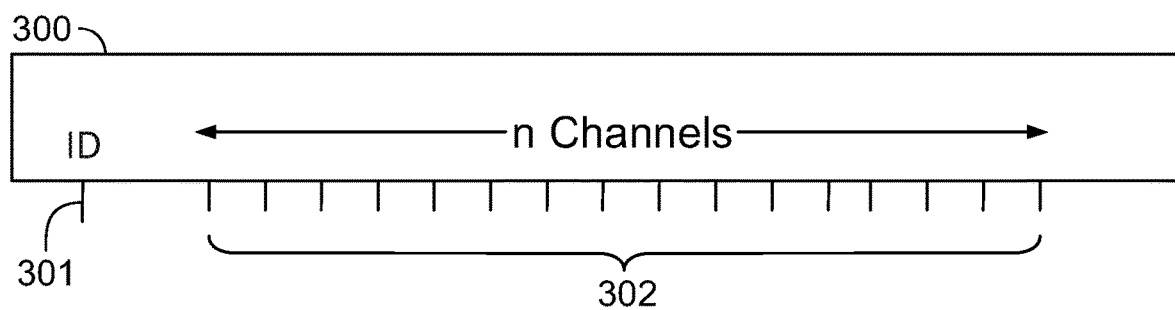
FIG. 3A shows an exemplary connector and a receiving socket in accordance with an embodiment of the present specification.
Figure 3A:
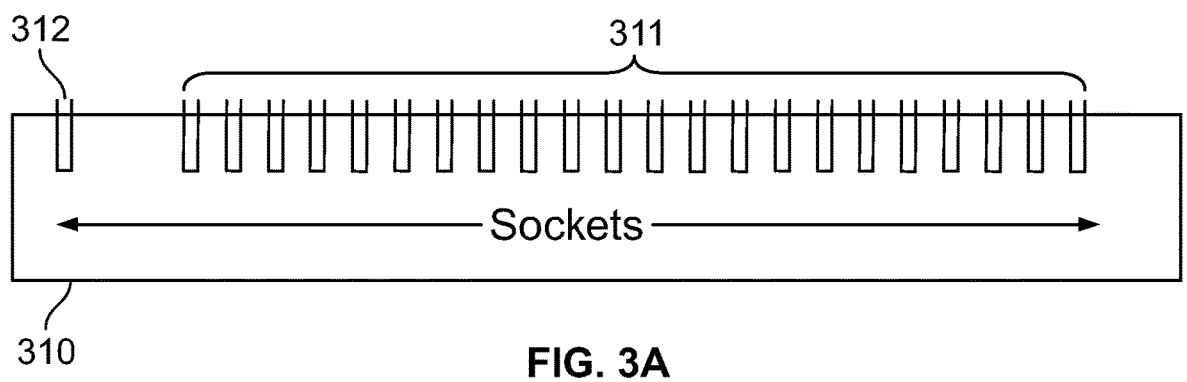

FIG. 3A shows an exemplary connector 300 and a receiving socket 310 in an embodiment. As shown in FIG. 3A, the connector 300 comprises a plurality of signal output pins 302 which corresponds to a plurality of electrodes (not shown) deployed on the body of the patient with the help of the connector 300. The connector 300 is coupled to the plurality of electrodes through one or more electrical leads (not shown). In some embodiments, the connector 300 is coupled to the electrodes through a wireless communication link. In embodiments, each connector, such as the connector 300, has a unique identity and is coupled to a plurality of electrodes which are included in the same group. In some embodiments, wired (via electrical leads) and/or wireless connections transmit the unique identity (such as GUID) and information about the electrodes, as well as signal data from the electrodes, to the system. In some embodiments, wherein the connection is wireless, transmission is directly from the wireless electrode to the system. In other embodiments, wherein the connection is wireless, transmission is from a wireless connector attached to each electrode and configured to broadcast information, including but not limited to, signal data and GUID, from the electrode to the system. When the electrodes are classified in the same group, it means their input signals are of the same type and their relative positions are fully defined. These electrodes are connected to the input terminals of the connector in a specific pre-defined order. FIG. 3A shows an 'n' channel connector 300, which means that the connector 300 can accommodate an electrode group with maximum number of n electrodes wherein n is any natural number. In commercial applications, the value of n is usually 4, 6, 8, 10, 12 and 16, such that the corresponding number of electrodes can be coupled to a single connector.

In an embodiment, the connector 300 comprises a specific identification (ID) output pin 301 which is used to establish the unique identity (ID) of the connector 300. The receiving socket 310 comprises a bank of signal input points or sockets 311 which are configured to receive the signal output pins 302 of the connector 300. Usually, a receiving socket, such as the receiving socket 310, comprises enough input points to receive multiple connectors. In practical applications involving high density electrodes, the number of input points is over 200. The receiving socket 310 is coupled to a control unit/amplifier (not shown) which is used to control the entire system. In an embodiment, the receiving socket 310 comprises a separate ID input socket 312 which is configured to receive the ID output pin 301 of the connector 300. The connector 300 is inserted in the receiving socket 310 such that the ID output pin 301 is received in the ID input socket 312 and the signal output pins 302 are received in a subset of signal input sockets 311. Referring to FIG. 3A, in some embodiments, the system includes a plurality of receiving sockets 310 and a plurality of connectors 300 wherein any connector 300 can be inserted into any receiving socket 310 such that the ID output pin 301 aligns with and inserts into a corresponding ID input socket 312.

Once the identity of the connector 300 is established, the system is able to identify the type and location of all the electrodes coupled to the connector 300 irrespective of the set of input sockets 311 in which the connector 300 is inserted. Once the electrodes are identified, the control unit coupled to the receiving socket 310 reconfigures the system to automatically correlate, associate, assign or map each electrode with its corresponding input channel.

Each of the connectors, such as the connector 300, has a unique ID (identity). This identification information is stored in the connector 300 and is accessible to the system from its identification (ID) output pin 301. The ID information specifies the type and relative location of each electrode in the connector 300. In embodiments, the ID field comprises a GUID (Globally Unique Identifier) which is a standard format comprising 128-bit data and is used as an identifier in the computer software. It may also contain other device specific information about the attached device. In some embodiments, the unique ID comprises radio-frequency identification (RFID), near-field communication (NFC), integrated circuit (IC) chip, barcode, quick response (QR) code, or optical encoding. In some embodiments, the unique ID comprises Global Unique Device Identification Database (GUDID) information, Global Trade Item Number (GTIN) information, or a universally unique identifier (UUID). In some embodiments, connectors are identified by mechanical lockout (unique connectors for a quantity of electrodes) or color coding. Once a GUID is assigned, each input can be uniquely identified thereafter. In embodiments, the GUID data is stored in an inbuilt memory device in the connector 300 and, optionally, the memory device is an EPROM storage device. In some embodiments, the GUID is a digital ID which stores additional metadata with the electrode such as checksums, productions dates and authenticity. In other embodiments, the same electrode information is stored using multiple pins used like dip switches (combinations=$2^n$, i.e. 3 connections would give 8 combinations), with a resistor whose value represents the input type (i.e. 10 combinations per resistor), with a multiple pin multiple resistor (100 combinations with 2 pins), or with a bar code that could be read automatically. In other embodiments, the identification information is communicated through an RFID stored in the connector.

In some embodiments, the unique ID (for example, GUID) of each connector is 'system-wide' across all medical device modalities or all neurological medical device modalities. In some embodiments, the unique ID is specific not only to EEG devices but also to at least intraoperative monitoring (IOM), sleep, and electromyography (EMG) devices. For example, in one embodiment, unplugging an implanted grid electrode connector from an EEG amplifier and plugging it into an IOM machine would result in the GUID from the electrode connector being used by the IOM machine to access all data and configuration settings for the electrode from the system and applying the data as appropriate to the acquisition, analysis, and display within the new modality.

Further, in some embodiments, each unique ID is associated with a value, such as a counter, that is stored in a memory accessible to the control unit and usable by the control unit to limit the number of uses of the connector. The number of uses of a connector are tallied in relation to the counter and saved by the system as data associated with the connector. In some embodiments, the controller unit uses the counter data to count the number of total lifetime uses to prevent the use of a potentially worn out connector or a connector that has reached the maximum number of sterilization cycles. In some embodiments, the maximum number of sterilization cycles is in a range of 5-20. In some embodiments, the maximum number of mechanical connections before a connector becomes worn out is in a range of hundreds to thousands of connections, depending on the type of connector being used. In some embodiments, the counter date is used to track the number of licensed uses of the connector. For example, in an embodiment, a customer purchases the use of a connector on five patients. The counter tracks the five patients and then the system disables the connector for use on further patients beyond the first five until additional licenses are purchased, or determines how much a customer should be charged for the usage. In some embodiments, the counter tracks the number of uses of a connector between preventative maintenance checks. In some embodiments, the counter tracks a total number of sterilization cycles.

In some embodiments, data stored and associated with each unique ID includes but is not limited to the information listed below such that all aspects of a system, patient, and procedure data related to a connector (and associated electrode(s)) are retained when a connection of the connector is changed (physically moved):

Patient association (which patient an electrode is connected to)
Display settings (how data from the associated patient is being displayed)

Configurations settings (how data from the associated patient is filtered, analyzed, referenced, and montaged prior to display) as elements that are associated with the unique ID Specific electrode make and model (part number, lot number, serial number, and manufacturer) and region (for example, lower left quadrant of a 64 electrode grid)

Electrode characteristics and limitations (for example, 'do not stimulate with this electrode', maximum current, and number of common references)

Electrode history, such as impedance history and failure history

In the embodiment shown in FIG. 3A, the connector 300 is shown as a male electrical connector and the corresponding receiving socket 310 is shown as a female electrical connector. In other embodiments, the connector is configured as a female connector and the receiving socket is configured as a male connector.

Figure 3B:
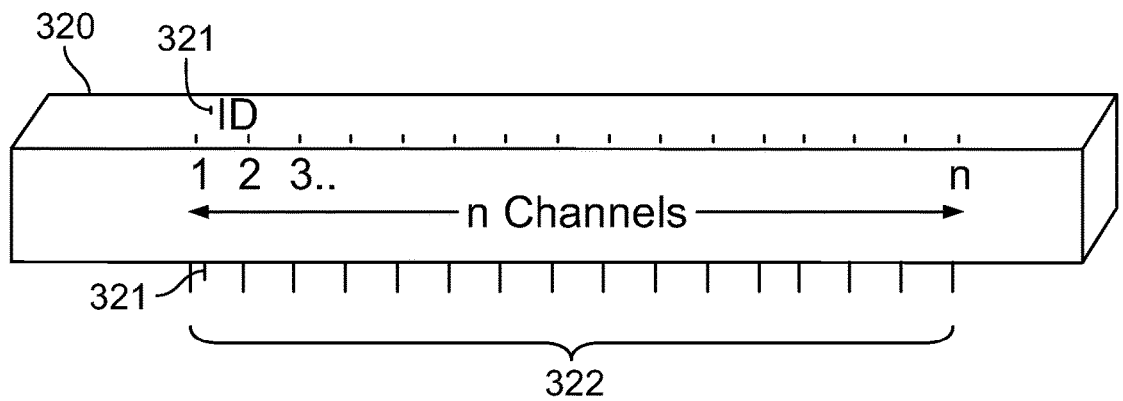
FIG. 3B shows an exemplary connector and a receiving socket in accordance with another embodiment of the present specification.
Figure 3B:
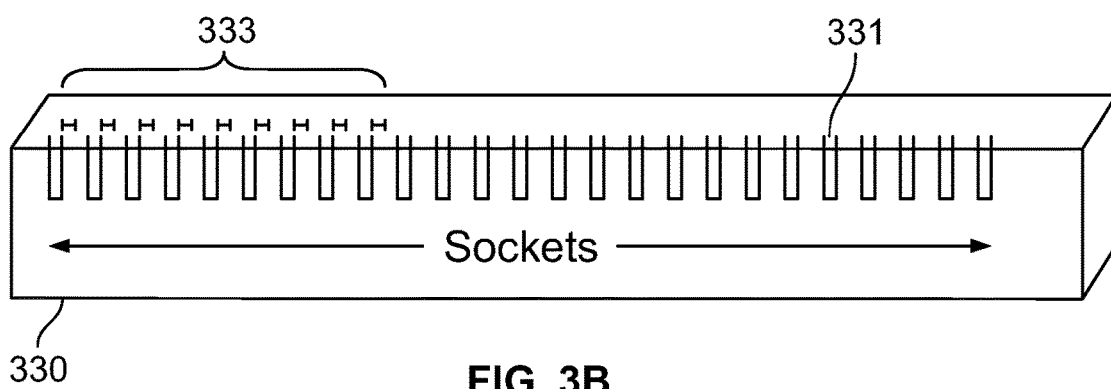

In another embodiment shown in FIG. 3B, the connector 320 is configured such that the ID output pin 321 is aligned parallel to, but not in series with, the set of signal output pins 322. The corresponding receiving socket 330 is configured such that instead of only one ID input socket, the receiving socket 330 comprises a plurality of ID input sockets 333 which are aligned parallel to the set of signal input sockets 331. The connector 320 and the receiving socket 330 shown in FIG. 3B are configured such that the connector 320 can be inserted in any of the input sockets 331 provided the ID output pin 321 is received by at least one of the ID input sockets 333.

The connectors and receiving sockets of the present specification are configured such that connections between the two are secure and reliable. In some embodiments, the connection between the connectors and receiving sockets is magnetically coupled. In some embodiments, the connection between the connectors and receiving sockets is direction independent such that the connectors are reversible about a horizontal plane. In some embodiments, the receiving sockets are configured to have sufficient depth such that inserted connectors cannot be removed by pulling on an attached cable sideways but only by pulling the connector straight out. With magnetic connectors, incorporating depth to the receiving sockets to restrict removal of the connector to only straight out maximizes the magnetic strength and keeps the connector connected unless a certain amount of force is used. The depth incorporated in the sockets depends on the geometry of the connector and varies by socket. In some embodiments, the receiving socket produces an audible 'click' when the connector is fully inserted to provide confidence that the connector is properly connected to the receiving socket. In addition, in various embodiments, all components of the systems of the present specification, including the connectors and receiving sockets, are designed mechanically to meet isolation and standoff requirements for shock hazard.

In some embodiments, not all of the available electrode channels on a connector might be used. For example, a 16 channel GUID connector might be used with a 10 channel electrode connected to it. In these instanced, the systems of the present specification provide for auto disabling of unused channels for standard electrodes and modified electrodes which do not display or store data. The systems will automatically detect disconnected channels or will, by reference from the configuration of the attached electrode either through direct association by the user or from information obtained directly from the ID of the electrode, know which connector channels are not physically connected to an electrode and will 'turn off' acquisition and display of the unused channels.

As discussed above, in some embodiments the connectors are associated with a GUID since. In prior art systems, electrodes are typically "off the shelf" and are associated with a color-coded identification for differentiating the placement of each electrode on the surface (or in a depth) of a patient's brain. However, such "off the shelf" color-coded electrodes do not have any machine-readable globally unique ID and are unique only to a case or patient.

Figure 3C:
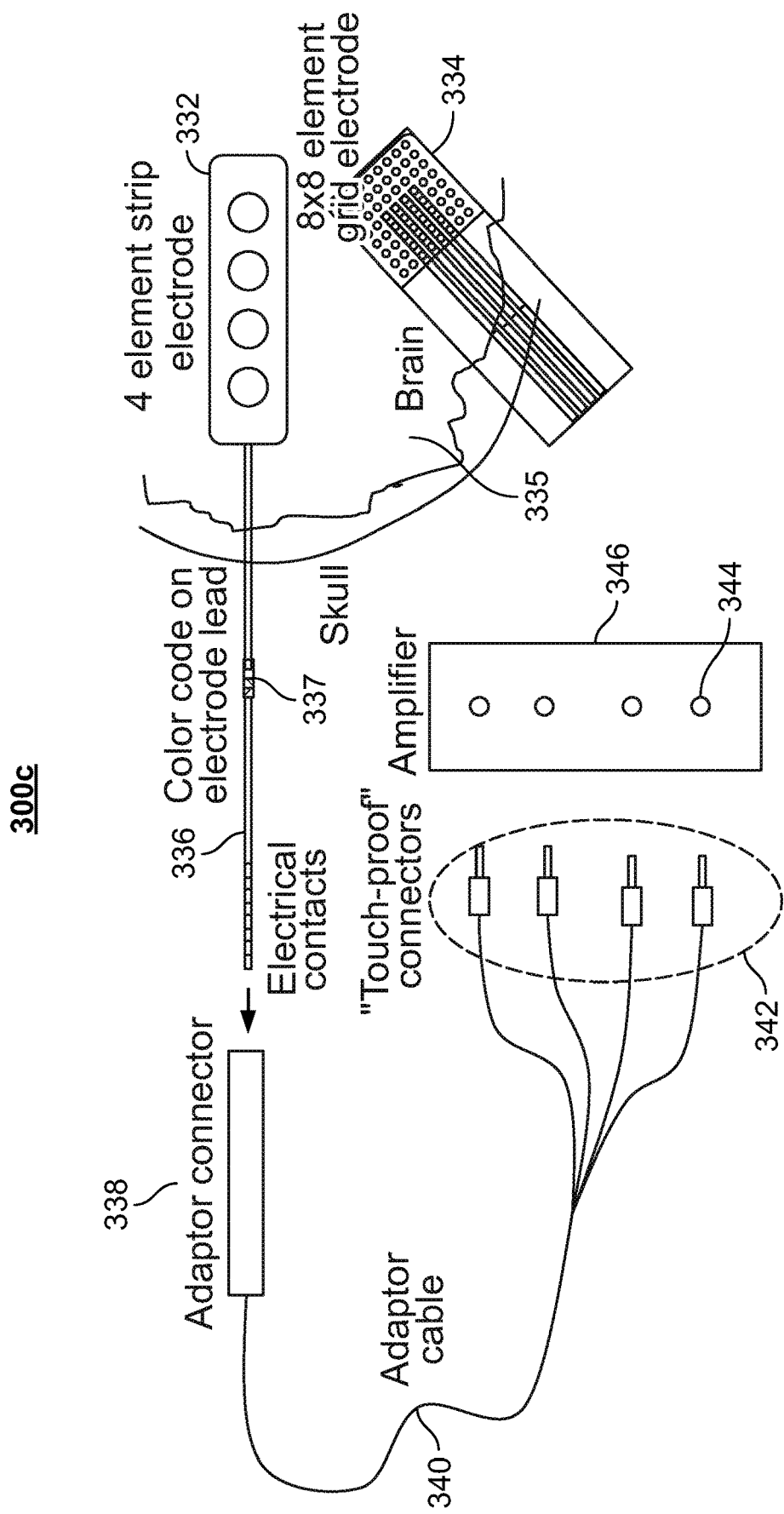
FIG. 3C illustrates a prior art system for connection of at least one electrode (or at least one group of electrodes) to an amplifier of a medical device in an embodiment.

FIG. 3C illustrates a prior art system 300c of connecting at least one electrode (or at least one group of electrodes) to an amplifier of a medical device in an embodiment. As shown, a 4-element strip electrode 332 and an 8×8 element grid electrode 334 are positioned within a patient's brain 335. In embodiments, in order to position on a patient's scalp (extracranial), a cap may be used. The electrode lead 336 from the 4-element strip electrode 332 is configured to be inserted into an adapter connector 338, which is configured for receiving electrode 332. The electrode lead 336 has a color-coded band or a numerical/alpha-numerical code 337 that uniquely identifies the electrode 332 for that particular patient but that is not globally unique (that is, each code is to be used only once). An adapter cable 340, emanating from the adapter connector 338, terminates into a plurality of "touch proof" connectors 342 that need to be manually mapped into appropriate jacks 344 on the amplifier 346. Thus, manual intervention is required.

During surgery, the strip electrode 332 is placed on the surface of the brain 335, the location of the strip electrode 332 is documented, and the color code or numerical/alpha-numerical code 337 associated with each electrode is recorded. In other words, in a cumbersome manual process, the user must read the color bands or codes 337, associate those colors or codes with the type of electrode the color bands or codes represent, and the location of the electrode on the brain (from a surgical case documentation). This is done while the brain is exposed via a craniotomy. After the surgery is complete, the craniotomy site is closed and the user can no longer see the electrodes, only the "pigtails" or the electrode lead 336 with color coded bands or codes 337 which indicate the nature and location of the electrode. In addition, when connectors 342 are removed from the amplifier 346 they must be manually remapped upon re-insertion. This procedure is slow and prone to errors. Mapping errors can lead to improper diagnosis and possibly an incorrect treatment including removal of the wrong portion of the brain during a surgical procedure.

Figure 3D:
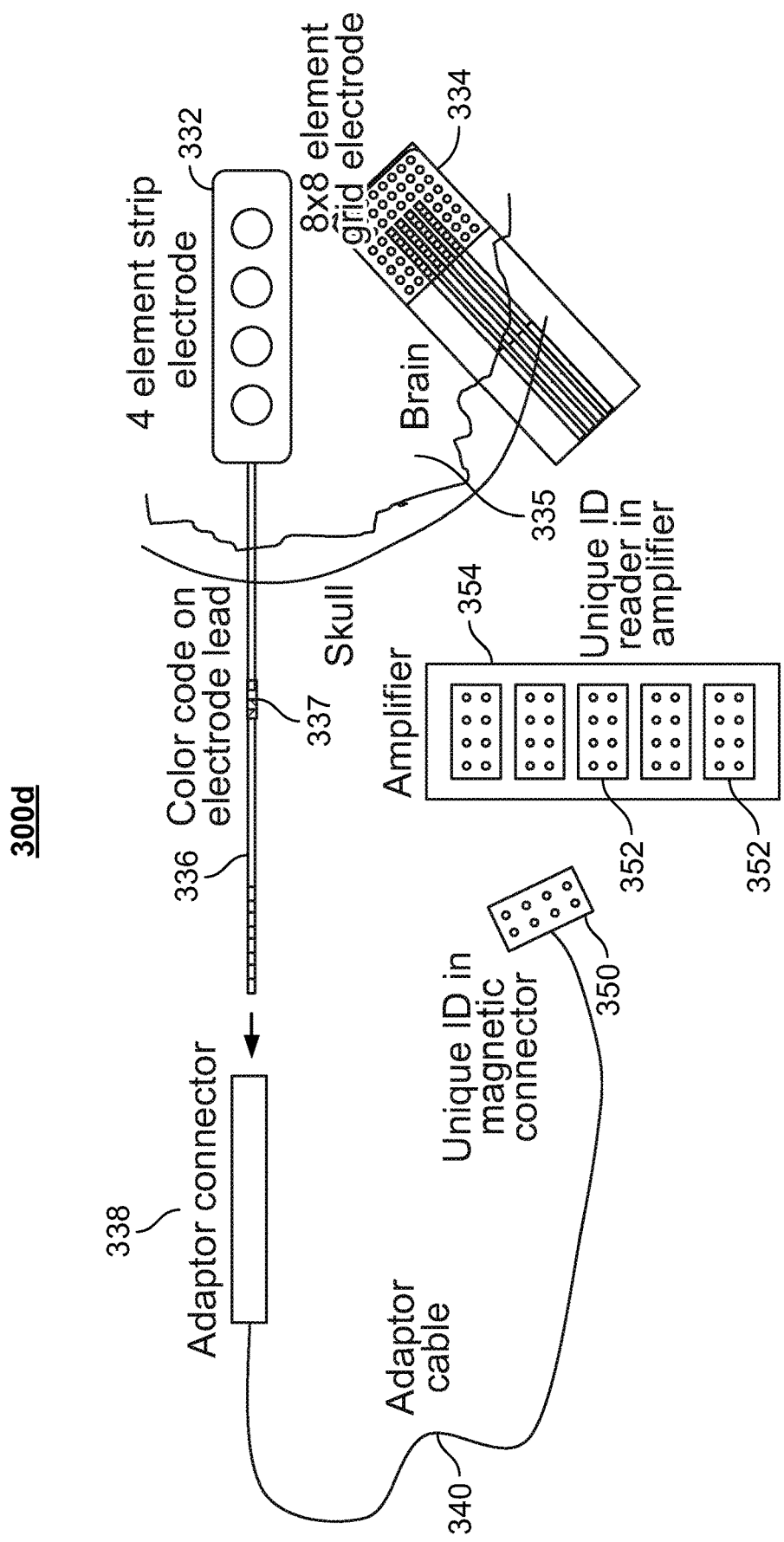
FIG. 3D illustrates a first embodiment of a system for connection of at least one electrode (or at least one group of electrodes) to an amplifier of a medical device, in accordance with some embodiments of the present specification.

FIG. 3D illustrates a first system 300d for connecting at least one electrode (or at least one group of electrodes) to an amplifier of a medical device, in accordance with some embodiments of the present specification. As shown, a 4-element strip electrode 332 and an 8×8 element grid electrode 334 are positioned on the surface of the patient's brain 335. In embodiments, in order to position on a patient's scalp (extracranial), a cap may be used. The electrode lead 336 emanating from the 4-element strip electrode 332 is configured to be inserted into the adapter connector 338 for electrical connection. The electrode lead 336 has a color coded band or a numerical/alpha-numerical code 337 that uniquely identifies the electrode 332 for the particular patient but that is not globally unique (that is, each code is to be used only once). An adapter cable 340, emanating from and in electrical and/or data communication with the adapter connector 338, terminates and is in electrical and/or data communication with a connector 350 that includes a GUID tag in accordance with some embodiments of the present specification. The connector 350 is inserted into any of the appropriate sockets 352 on the amplifier 354. In embodiments, sockets 352 are universal sockets. In embodiments, connectors 350 may vary in size such that one connector 350 may fit into a plurality of sockets 352. For example, a connector 350 may, in embodiments, be twice the original width and therefore may be received by two sockets 352.

In accordance with an aspect, the amplifier 354 includes a reader (not shown) to detect the GUID tag in the connector 350 and acquire a plurality of information stored in the GUID tag. Once the connector 350 is inserted into one of the sockets 352, the system 300d recognizes that a new connector 350 has been connected to the amplifier 354 and the user is prompted to identify what was connected. Thus, if an unrecognized GUID is inserted into a socket 352, the system, via the GUI, prompts the user to identify the electrode that was connected. The user accesses at least one GUI (Graphical User Interface) that enables the operator to select from a plurality of pre-programmed electrode types (or enter customized types). Specifically, in an embodiment, the user may select from a drop-down list of possible electrodes. In one embodiment, the drop-list prompts the user to identify the electrodes by manufacturer part number. In some embodiments, electrodes may have multiple leads as is shown by grid electrode 334. In such cases, the user will need to identify both the correct manufacturer part number and the correct lead number (for example, 1-4). The GUI also provides a unique and simple interface to associate a color code or alphanumeric ID to the electrode for reference.

U.S. patent application Ser. No. 16/697,850, entitled "Methods for Automatic Generation of EEG Montages" and filed on Nov. 27, 2019, also by the Applicant of the present specification, is herein incorporated by reference in its entirety. Once an association has been made between the unique ID in the connector 350 and electrode 332, the connector 350 may be moved to a different socket 352 on the amplifier 354 or even to a different amplifier altogether and the system 300d will still "know" (as the information is stored in the system) what is connected and how to map the data appropriately within the software application of the medical device. Thus, once the identity of the connector 350 is established, the system is able to identify the type and location of all the electrodes (or group of electrodes) coupled to the connector 350 irrespective of the set of input sockets 352 in which the connector 350 is inserted. In embodiments, adapter connector 338 and adapter cable 340 which emanates from and is in electrical and/or data communication with the adapter connector 338 and which terminates and is in electrical and/or data communication with a connector 350 are reusable. It should be noted that once mapping information is erased, the assembly, which include adapter connector 338, adapter cable 340, and connector 350 may be sterilized and a new mapping may be created for the same GUID on the next patient. Thus, if the electrode lead 336 is removed from the adapter connector 338, then the user will need to re-map which electrode is connected to the adapter connector when re-connected once mapping information is intentionally deleted. If the electrode lead 336 is removed from the adapter connector 338, and then re-inserted into the same adapter connector 338, the mapping will remain in the system memory.

Figure 3E:
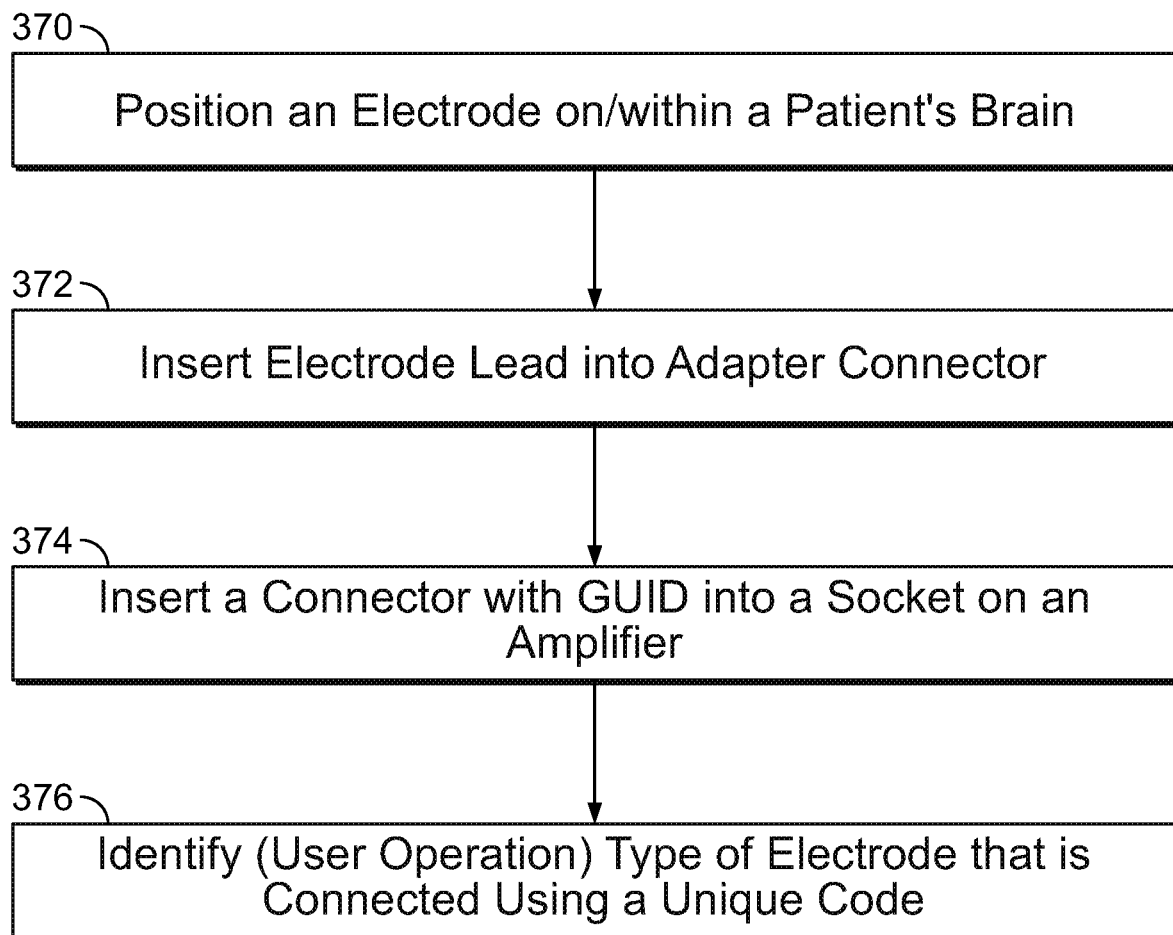
FIG. 3E is a flow chart showing steps in a method for using the first embodiment of a system for connection of at least one electrode (or at least one group of electrodes) to an amplifier of a medical device, in accordance with some embodiments of the present specification and as shown in FIG. 3D.

FIG. 3E is a flow chart showing steps in a method for using the first embodiment of a system for connection of at least one electrode (or at least one group of electrodes) to an amplifier of a medical device, in accordance with some embodiments of the present specification and as shown in FIG. 3D. At step 370, a 4-element strip electrode and/or an 8×8 element grid electrode are positioned on or within the patient's brain. The electrode lead emanating from the 4-element strip electrode is inserted into the adapter connector for electrical connection at step 372. A connector, which is in electrical and/or data communication with the adapter connector via an adapter cable is inserted, at step 374, into an appropriate socket on an amplifier. Once the connector is inserted into one of the sockets, the system recognizes that a new connector has been connected to the amplifier and the user is prompted to identify what was connected, in step 376.

In various embodiments, the connector 350 is magnetically coupled with the sockets 352. In various embodiments, the connection between the connector 350 and receiving sockets 352 is direction independent such that the connectors are reversible about a horizontal plane. In embodiments, the connector 350 may vary in size to optimally match the number of leads on the electrode. In embodiments, there may be unused pins of receiving sockets 352 depending on which electrode is connected. In embodiments, pins on connector 350 may be used to transmit GUID data.

In some embodiments, a pigtail ID tag or pigtail GUID tag is added to a lead of an electrode to provide means of identifying and storing information related to the electrode. In other embodiments, an ID tag is associated to an electrode by other connection means, such as a wireless RF (Radio Frequency) or an optical connection. In various embodiments, the pigtail ID tag is applied to the electrode before, during, or after a surgical procedure. In other embodiments, the pigtail ID tag is added to an electrode by the manufacturer prior to use. In embodiments, the pigtail ID tag is used to associate an electrode with a GUID connector (such as connector 365 as described below). A computing device, such as a tablet, PC, phone, watch, or other electronic means is used to scan the pigtail ID tag during a surgical procedure and enter appropriate information into the system by a user, such as but not limited to:

Electrode type and attributes (model, lot, electrode numbers, size, configuration, expiration date, and default montage)

Location and orientation in the brain including electrode depth

Color coding or other labeling from the manufacturer

The pigtail ID tag is then later scanned when connected to an amplifier of a GUID connecter to create an association between the electrode and connector. All information gathered during the surgical procedure is automatically associated with the GUID connector. Electrodes may be disconnected from a first associated GUID connector (for example, when a patient needs to undergo an MIll scan) and the association procedure may repeated on any other appropriately sized GUID connector. In other words, the patient does not need to be connected to the same first associated GUID connector. All data associated with the pigtail ID tag for the electrode would now be associated seamlessly to the new GUID connector. In some embodiments, the association is confirmed via a graphical display to the user. In embodiments where the pigtail ID tag is received pre-attached to the electrode directly from the manufacturer (instead of being added before, during, or after a surgical procedure), the pigtail ID tag already contains the electrode attribute information listed above and the information does not need to be entered by the user. In some embodiments, the pigtail ID tag, or a similar ID tag, is used to identify any and all other accessories or devices attached to the system, including but not limited to, a surgical stimulation probe, expansion headbox, and stimulation box.

Figure 3F:
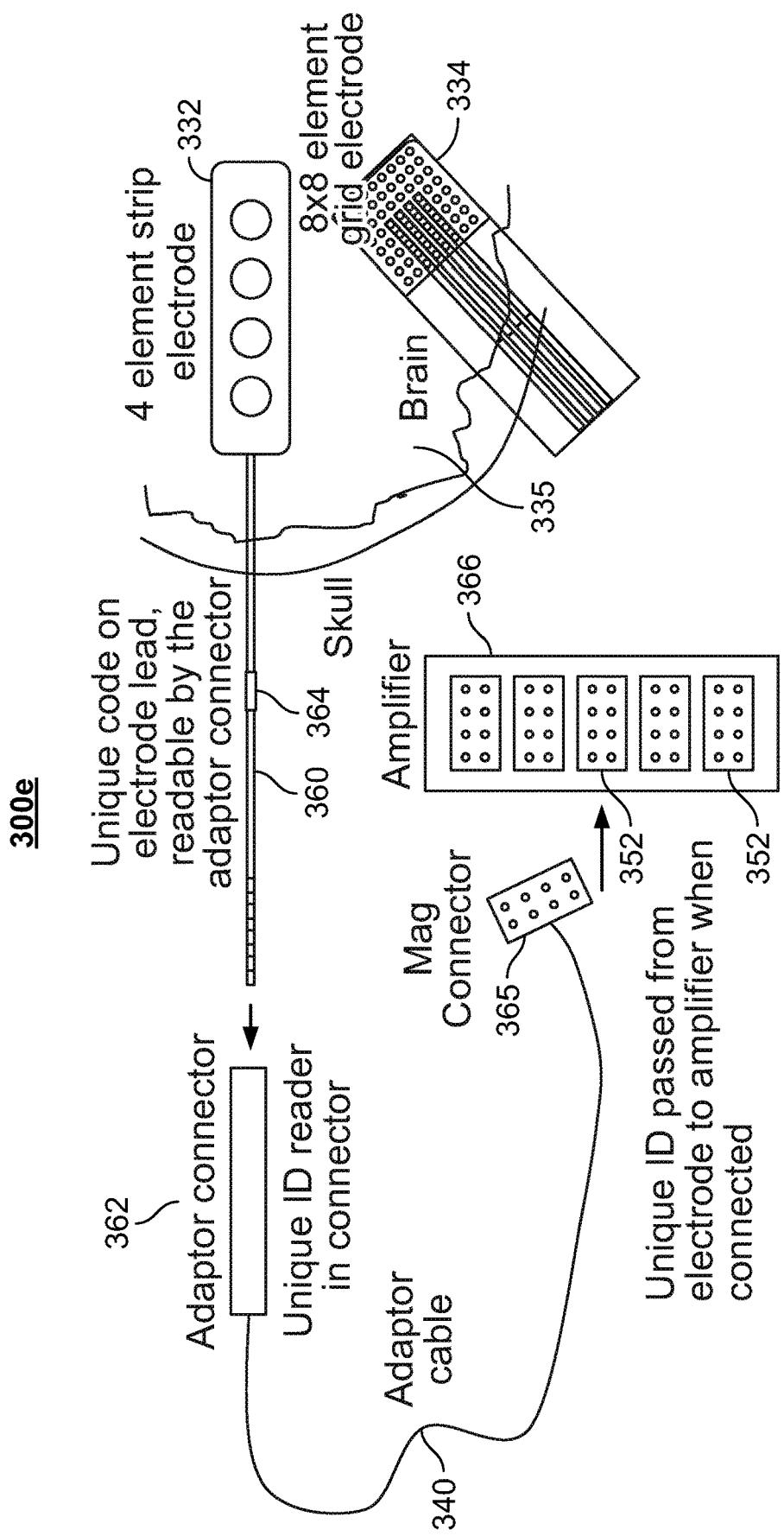
FIG. 3F illustrates a second embodiment of a system for connection of at least one electrode (or at least one group of electrodes) to an amplifier of a medical device, in accordance with some embodiments of the present specification.

FIG. 3F illustrates a second system 300e for connection of at least one electrode (or at least one group of electrodes) to an amplifier of a medical device, in accordance with some embodiments of the present specification. As shown, the 4-element strip electrode 332 and the 8×8 element grid electrode 334 are positioned on/within the patient's brain 335. An electrode lead 360 from the 4-element strip electrode 332 is configured to be inserted into an adapter connector 362 for electrical connection. In accordance with an aspect of the present specification, the electrode lead 360 carries a "pig tail" unique ID (GUID) tag 364. The adapter cable 340, emanating from and in electrical and/or data communication with the adapter connector 362, terminates into and is in electrical and/or data communication with a connector 365. The connector 365 is inserted into any of the appropriate sockets 352 on the amplifier 366.

In some embodiments, the tag 364 is embedded into the electrode lead 360 such that it may be read directly by the adapter connector 362. Thus, in accordance with an aspect of the present specification, the adapter connector 362 includes a reader to detect the GUID tag in the electrode lead 360 (which is inserted into the adapter connector 362) and acquire a plurality of information stored in the GUID tag 364 that is passed through the connector 365 to a software application associated with the medical device. Once the connector 365 is inserted into one of the sockets 352, the system 300e recognizes that a new connector 350 has been connected to the amplifier 354 and the unique ID tag 364 is read directly by the software application associated with the medical device. In embodiments, GUID data is communicated via the amplifier and processed by a software application running on the computing system to which the amplifier is connected. In alternate embodiments, the software application resides on the amplifier itself. In embodiments, the unique ID tag 364 is used to configure display and other settings using knowledge of the geometry and type of the connector 365.

In alternate embodiments, the tag 364 is configured as a crimp, an adhesive label or an adhesive wrap around "flag" that requires a barcode reader to be read, for example. In this case the user may scan the electrode (for the tag 364) and then scan the adapter connector 362 to associate the two. In various embodiments, the tag 364 comprises a bar code, QR code or an RFID code.

Because the system 300e essentially "reads" the unique ID tag 364 from the electrode 332 and because the ID is globally unique, the system 300e can use the unique ID to "look up" (within a database) required properties of and information (such as, but not limited to, manufacturer, number of electrodes, geometry, materials, and any special considerations) about the electrode 332 from the manufacturer and automatically configure the system 300e appropriately. The user would still need to document the location of the electrode 332 on the surface of the brain, but all other steps are eliminated.

If the electrode 332 is removed from the connector 365 and inserted into a different connector, the system 300e will automatically read the ID tag 364 and perform the appropriate association without requiring user intervention. Also, it should be appreciated that the unique ID 364 from the electrode 332 is read whenever the connector 365 is moved or connected to a different amplifier to resume data collection and display without the need for manual configuration.

Figure 3G:
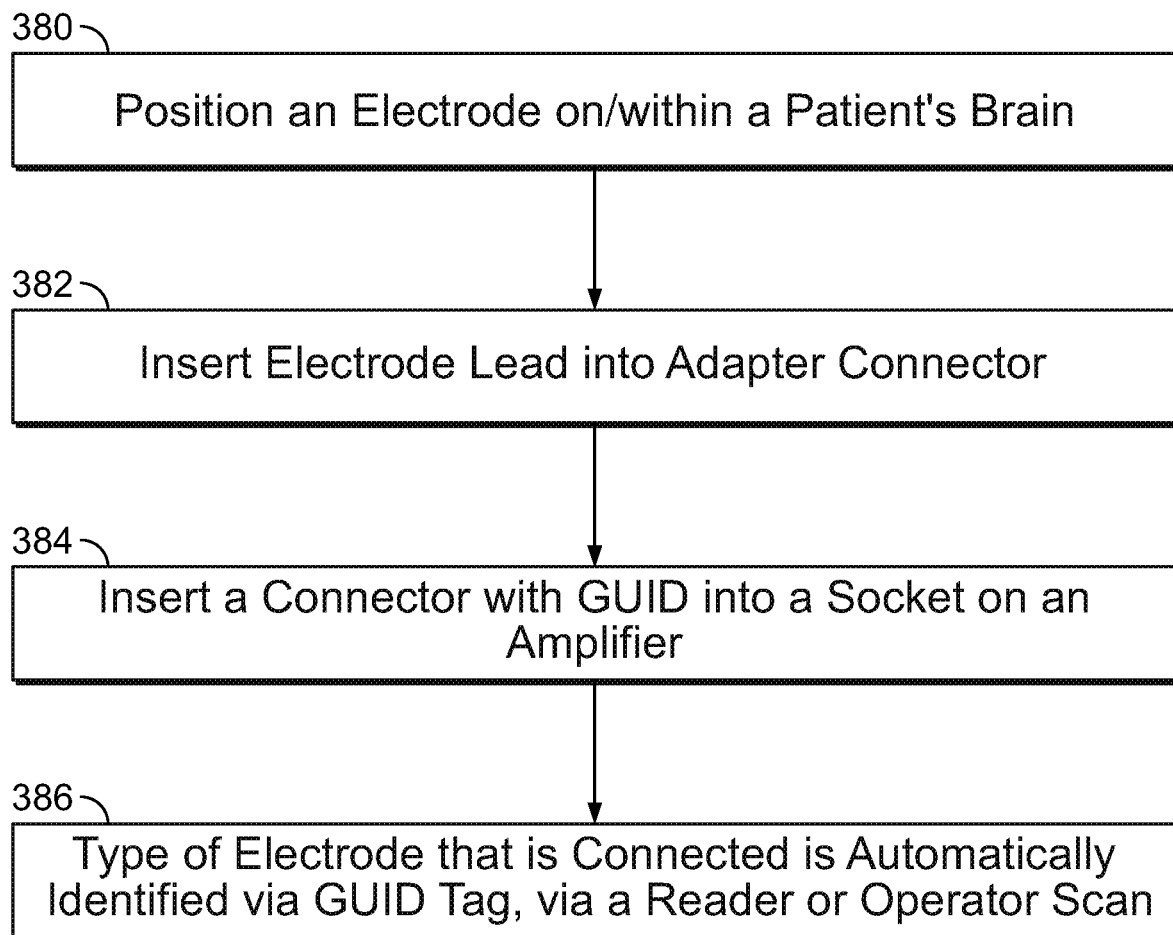
FIG. 3G is a flow chart showing steps in a method for using the second embodiment of a system for connection of at least one electrode (or at least one group of electrodes) to an amplifier of a medical device, in accordance with some embodiments of the present specification.

FIG. 3G is a flow chart showing steps in a method for using the second embodiment of a system for connection of at least one electrode (or at least one group of electrodes) to an amplifier of a medical device, in accordance with some embodiments of the present specification. At step 380, a 4-element strip electrode and/or an 8×8 element grid electrode are positioned on or within the patient's brain. The electrode lead emanating from the 4-element strip electrode is inserted into the adapter connector for electrical connection at step 382. A connector, which is in electrical and/or data communication with the adapter connector via an adapter cable is inserted, at step 384, into an appropriate socket on an amplifier. Once the connector is inserted into one of the sockets, the system recognizes that a new connector has been connected to the amplifier and automatically identifies or "reads" the electrode that is connected in step 386. In embodiments, the tag may be read directly by the adapter connector. In alternate embodiments, the user may scan the electrode for the tag and then scan the adapter connector 362 to associate the two, where the tag may be a bar code, QR code or an RFID code.

In various embodiments, the connector 365 is magnetically coupled to the sockets 352. In various embodiments, the connection between the connector 365 and receiving sockets 352 is directionally independent such that the connectors are reversible about a horizontal plane. In embodiments, the connector 365 may vary in size to optimally match the number of leads on the electrode.

It should be noted that in medical procedures, the electrodes are classified in groups wherein the electrodes belonging to the same group are of similar type and are deployed in a similar location. In EEG procedures, the electrodes typically come in groups of 4, 5, 6, 8, 10 and 16 electrodes, although other groupings are also used, wherein each such group is targeted towards a specific part of the brain. If connectors of the same size are used for all electrode groups, several input channels will go to waste in the case of connectors that are mapped to groups having fewer numbers of electrodes. To allow high utilization of input channels, in embodiments, the electrodes are organized in small groups and the connectors are designed in different sizes which provide the flexibility to support the electrode groups of varying sizes.

FIG. 4A illustrates connectors 410, 420, 430, 440 of different sizes. As shown in FIG. 4A, connector 410 comprises an ID output pin 401 and a set of four output pins 402 which can support an electrode group comprising up to four electrodes. Connector 420 comprises eight output pins 422 so in case the number of electrodes is more than four and less than or equal to eight, the user can deploy connector 420 instead of the connector 410. Similarly, connector 430, having 12 output pins can support up to 12 electrodes and connector 440, having 16 output pins, can support up to 16 electrodes. Connectors 420, 430, and 440 also include ID output pins 421, 431, and 441 respectively. Instead of using connectors of a single size, the user can deploy connectors of multiple sizes, thereby reducing the space requirement in actual procedures. All the connectors have an ID output pin 401, 421, 431, 441 which is used to identify the unique identity of a connector which the system will use to correlate, assign, or associate all electrodes mapped through a connector with their correct channels. In some embodiments, referring to connectors 420, 430, and 440, the output pins are grouped into groups of four channels. For example, connector 420 includes two four-pin groups 422a and 422b of output pins 422, connector 430 includes three four-pin groups 432a, 432b, and 432c of output pins 432, and connector 440 includes four four-pin groups 442a, 442b, 442c, and 442d of output pins 442. A receiving socket is capable of accepting any of the connectors to be plugged in anywhere along its bank of inputs. Each connector needs only a single ID and the socket is configured to identify any connector in any position.

In some embodiments, systems of the present specification include a consolidator which functions as one single mass connector for connecting a multitude of electrodes. A consolidator comprises a single mass termination connector or connection plate to which a plurality of connectors, such as connector 300 of FIG. 3A, connector 320 of FIG. 3B, and connectors 410, 420, 430, 440 of FIG. 4A, are configured to be connected. The consolidator is configured to be connected to or removed from an amplifier of a monitoring system as a single unit. In some embodiments, connectors of different sizes and having different numbers of output pins may be inserted into a consolidator simultaneously. All unique ID (for example, GUID) data from each individual connector is transferred through the consolidator to the amplifier.

Figure 4C:
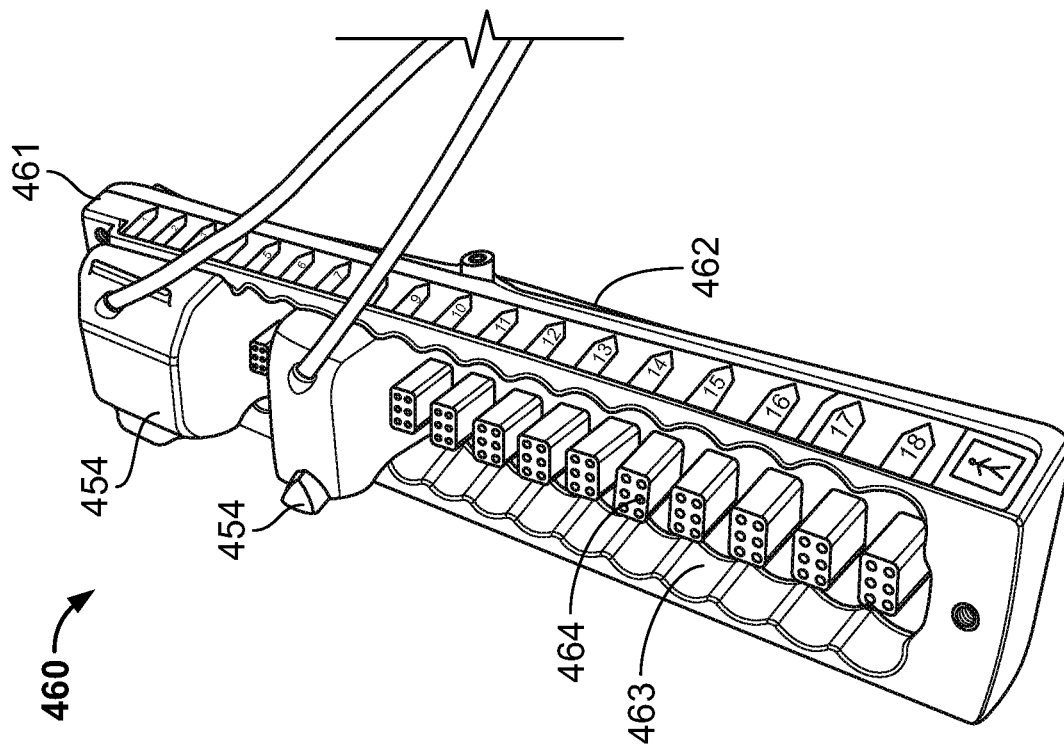
FIG. 4C illustrates a second consolidator for receiving a plurality of connectors, in accordance with some embodiments of the present specification.
Figure 4B:
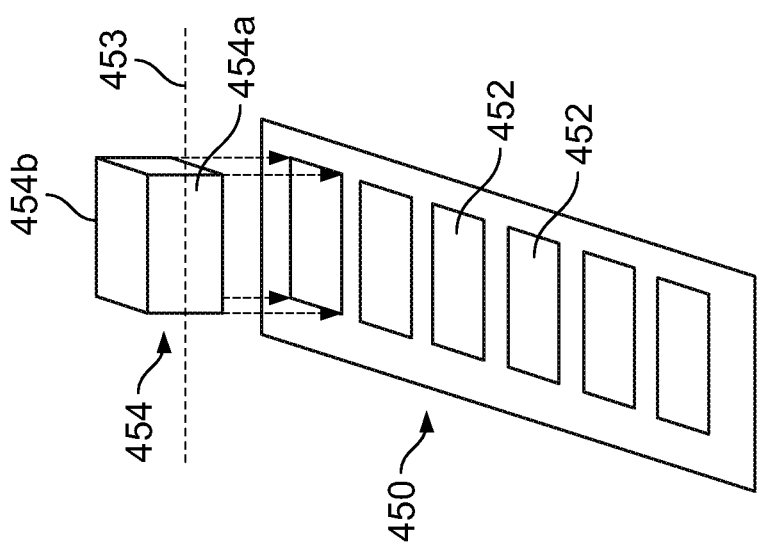
FIG. 4B illustrates a first consolidator for receiving a plurality of connectors, in accordance with some embodiments of the present specification.

FIG. 4B illustrates a consolidator 450 for receiving a plurality of connectors, in accordance with some embodiments of the present specification. As shown, the consolidator 450 is a flat plate or module of a suitable insulating yet rigid material (such as, but not limited to, plastic) with a plurality of openings or holes 452 cut therein that attach to and correspondingly hold a plurality of connectors, such as the connector 454. During operation, the connector 454 is partially inserted into the opening or hole 452 of the consolidator 450 to a point 453 where a first portion 454a (comprising a plurality of output pins) of the connector 454 protrudes below the consolidator 450 and a second portion 454b (comprising a handle portion) extends above the consolidator 450.

The consolidator 450 may then be used to hold/contain a plurality of connectors for one side of an amplifier with a user inserting and removing all connectors at once using the consolidator 450. In this case, "transfer" of the ID and other signal data does not need to happen through the consolidator 450 as in this embodiment the consolidator 450 is a mechanical means of positioning multiple connectors so they may be inserted into and removed from the amplifier simultaneously, if needed.

FIG. 4C illustrates a consolidator 460 for receiving a plurality of connectors 454, in accordance with some embodiments of the present specification. As shown, the consolidator 460 is configured as a plate or module 461 comprising a plurality of male connector elements on a first side 462 that are configured to be connected to connector receptacles on an amplifier (not shown). The consolidator 460 also includes a plurality of female receptacles or sockets 464 on a second side 463, opposite the first side, for receiving male connector elements of connectors 454. The male connector elements on the consolidator 460 are similar to, or match, the male connector elements of the connectors 454 and the female receptacles on the amplifier are similar to, or match, the female receptacles 464 on the consolidator 460. During use, the connectors 454 are first inserted into the consolidator 460, by connecting the male connector elements of the connectors 454 with the female receptacles or sockets 464 of the consolidator, and then the consolidator 460 is subsequently inserted into the amplifier by connecting the male connector elements of the consolidator 460 with the female receptacles of the amplifier (shown in FIG. 4D). In this manner, the consolidator 460 connects to or detaches from the amplifier as a single unit. In this embodiment, each electrical connection in the consolidator 460 passes through from each receptacle 464 to the amplifier. Thus, the connectors 454 make electrical contact with the female receptacles 464 and the electrical connection is passed through the consolidator 460 to male connector elements that insert into the female receptacles on the amplifier. In some embodiments, the consolidator is in electrical and/or data communication with both the connectors and the amplifier.

Also shown in FIG. 4C is an actual implementation of the system shown in FIGS. 3D and 3F. In an embodiment, a plurality of sockets 464 each contains 6 contact pins, two of which are used to communicate electrode data. Thus, in this embodiment shown, two sockets 464 are used to read 8 channels. In an example with a 2×5 grid (a 10-channel grid), three blocks would be needed (for a total of 12 channels available as 6 are used for communicating electrode data), although only 10 pins/channels would be employed. In embodiments, multiple sizes of connectors 454 can be employed.

Figure 4D:
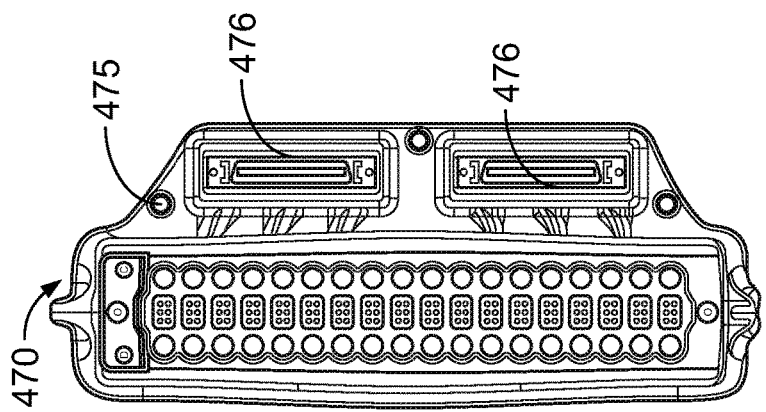
FIG. 4D illustrates the electrical connections of the consolidator shown in FIG. 4C housed in a bracket for data communication with a third party device, in accordance with some embodiments of the present specification.
Figure 4D:
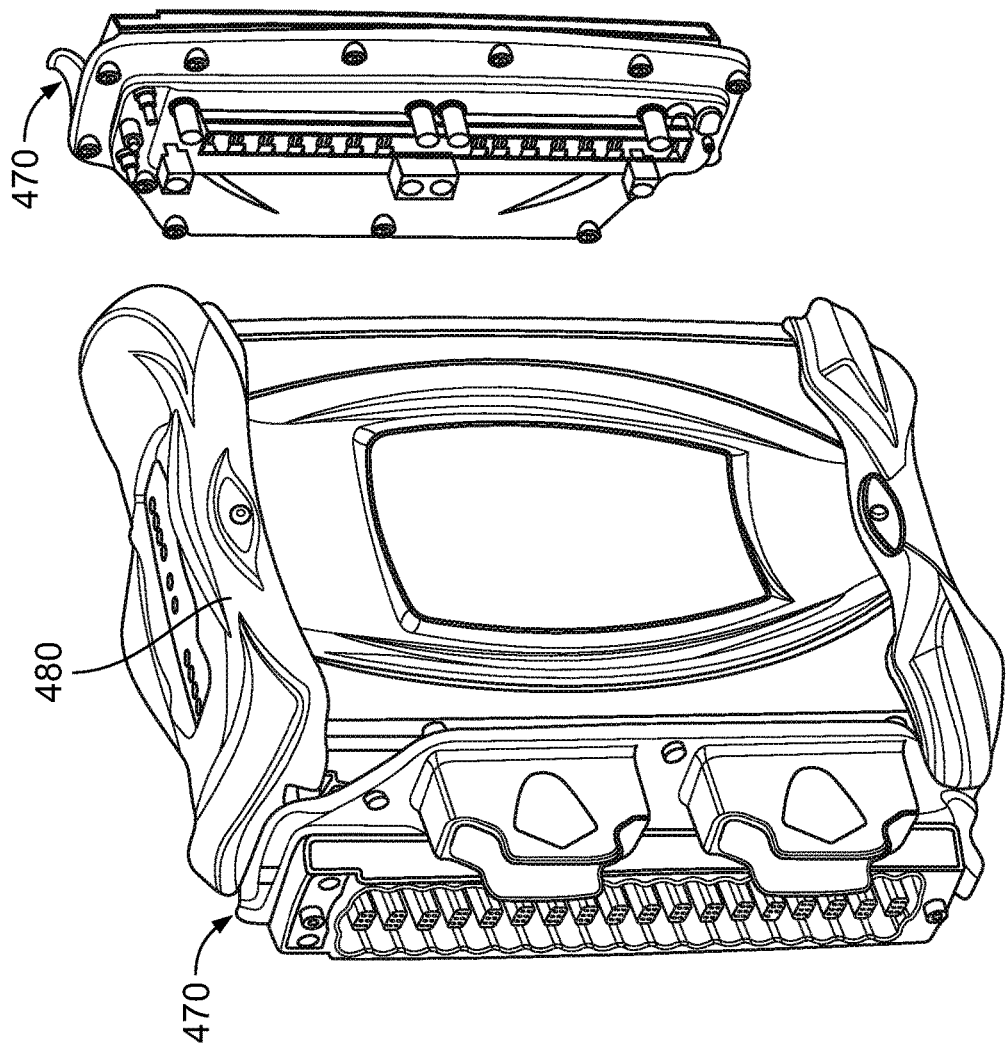

FIG. 4D illustrates a consolidator 470 for receiving a plurality of connectors, in accordance with other embodiments of the present specification. The consolidator 470 is housed in a bracket 475 for data communication with a third party device, in accordance with some embodiments of the present specification. Each consolidator 470 may be housed in a bracket 475 wherein the bracket enables connection to a third party device either through passive or active (amplified) means. Thus, the signals may be sent directly to a third party device. In addition, bracket 475 comprises two bracket connectors 476 that may be placed in electrical communication with a third party device. In one embodiment, the consolidator 470 comprises male connector elements and female receptacles, similar to the consolidator 460 of FIG. 4C, to connect to the amplifier 480, and the bracket connectors 476 are in electrical communication with the amplifier and third party device through the male connector elements and female receptacles of the consolidator 470. In another embodiment, the bracket 475 is removable from the consolidator 470 and comprises or supplies a plurality of male connector elements on one side configured to connect with the connector receptacles on the amplifier. Further bracket 475 comprises female receptacles on the other side for receiving the male connector elements of the consolidator 470. Thus, in this embodiment, bracket 475 acts as a removable "bridge" from the consolidator 470 to the amplifier that enables connection of the consolidator to a third party device obviating the need for disconnection. Also, in this embodiment, bracket connectors 476 are in electrical communication directly with the amplifier and third party device through the male connector elements and female receptacles of the bracket 475.

It should be appreciated that in both embodiments of FIGS. 4C and 4D, the "transfer" of both ID data and signal data is a seamless direct pin-to-pin pass through on the connector. The system will see the same data on the same line as it would if the connector where plugged in directly to the amplifier.

In embodiments, connectors and the corresponding receiving socket comprise mechanisms to ensure that there is no misalignment when the connector is coupled with the receiving socket. In embodiments, multiple connector types are provided to be used with different kinds of products. In embodiments, certain inputs of the connectors are provided with enhanced capabilities, such as lower noise, higher offset voltage tolerance or differential inputs, and the user is required to plug inputs needing such capabilities into a subset of connector locations. In some embodiments, not every input has the same requirements and the amplifier or signal processing needed is different for those inputs. If the physical connector is inserted into an input whose channel did not support the function, then the system could notify the user to choose a different input that did support the function. In some embodiments, the system includes a subset of channels that have more capability and could accept either normal or enhanced inputs. These channels would still support non-enhanced inputs to allow better channel utilization. In some embodiments, $SpO_2$ or otherwise not supported input types are configured to a small number of inputs. In other embodiments, pressure inputs, for example, plug into a different bank of identified connectors set up for pressure measurements instead of voltage measurements.

In embodiments, apart from the unique ID, certain other information is stored in the connectors, such as the authentication information, production dates of the connector and the electrodes corresponding to each connector.

Figure 5A:
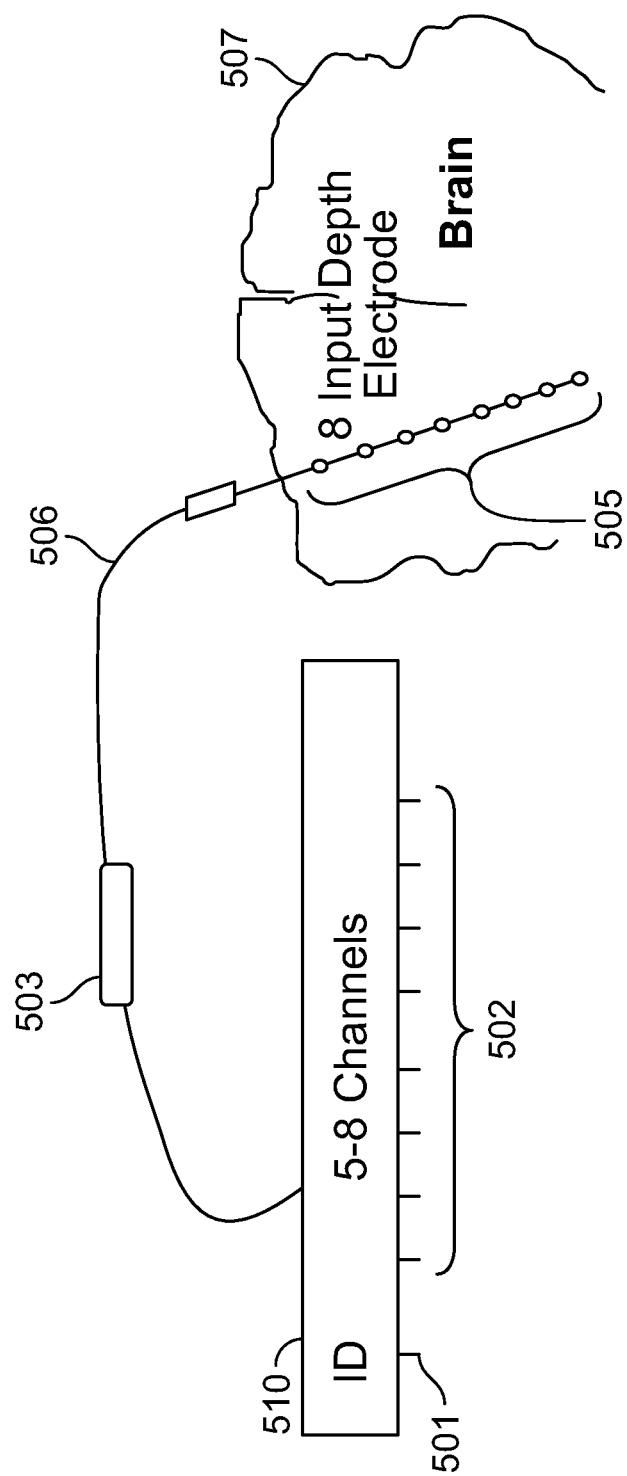
FIG. 5A shows an exemplary illustration of an eight channel connector deployed to support an eight input depth electrode in an EEG procedure in accordance with an embodiment of the present specification.

FIG. 5A shows an exemplary illustration of an eight channel connector 510 deployed to support an eight input depth electrode 505 in an EEG procedure. As shown in FIG. 5A, the connector 510 comprises an ID output pin 501 and a set of eight output pins 502 which means that the connector 510 can support up to eight electrodes. The connector 510 is coupled to an eight input depth electrode 505 through a set of electrical leads 506. In some embodiments, the depth electrode 505 is coupled to the connector 510 via one or more intermediate connectors 503. The intermediate connectors 503 provide the system with greater flexibility when dealing with the limited geometry involved in surgical procedures. In other embodiments, the system does not include intermediate connectors and the electrodes couple directly with the connector and the ID information is very specific to the electrode (for example, electrode caps, respiratory belts, and EKG inputs). The depth electrode 505 is positioned in the cortex area of the brain 507. The connector 510 has a unique ID (identity) stored in an inbuilt memory. In an embodiment, the unique ID comprises a 128 bit GUID and is stored in an EPROM (erasable programmable read-only memory) device in the connector 510. When the connector 510 is plugged in a receiving socket, the system reads the ID information from the EPROM memory device through ID output pin 501 and establishes the identity of the eight input depth electrode 505 coupled to the connector 510. The system accordingly configures itself (and reconfigures itself if the connectors are removed and re-inserted in another position) to correlate or associate the correct inputs of the depth electrode 505 with their corresponding input channels.

Figure 5B:
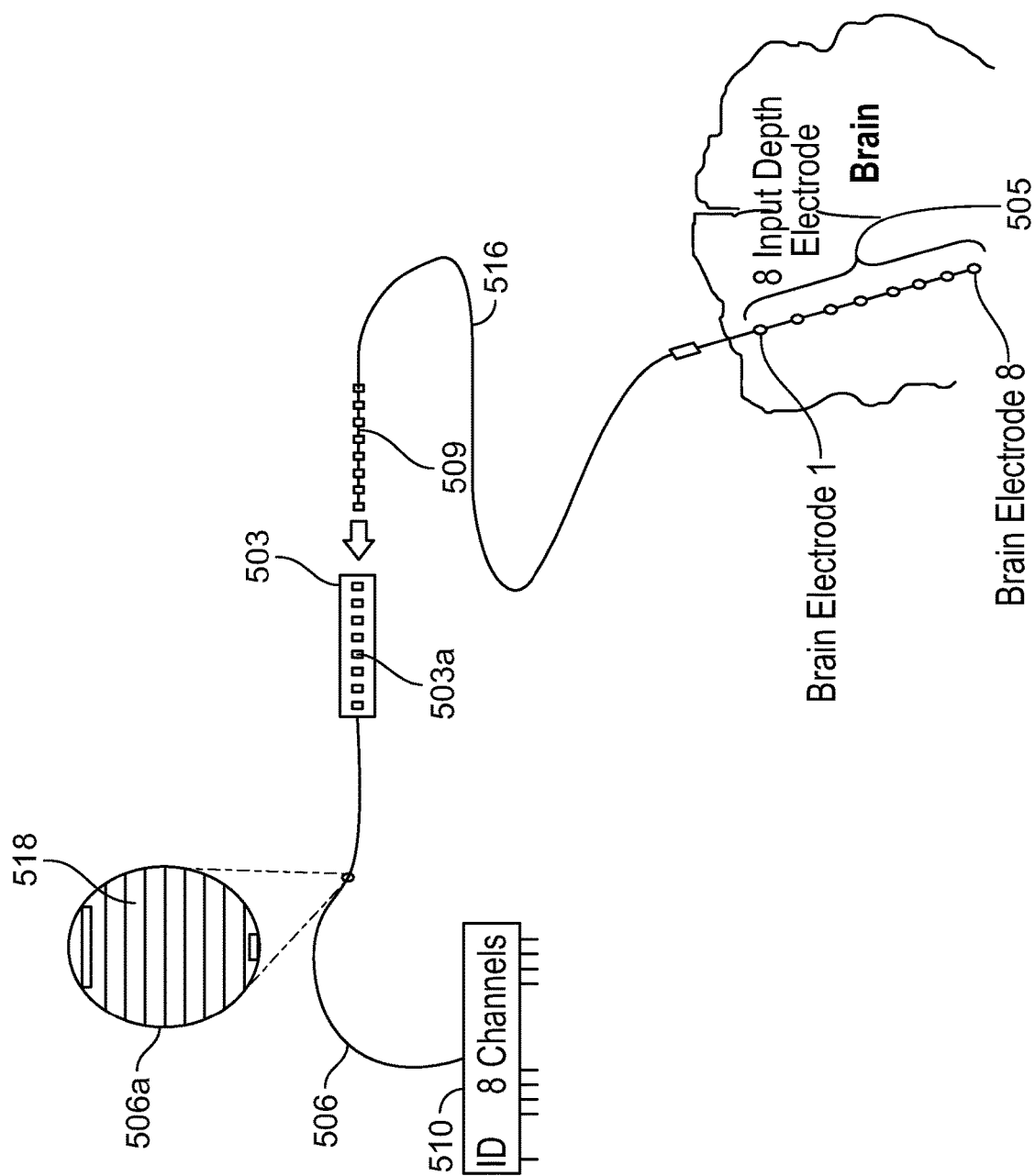
FIG. 5B shows a detailed illustration of the eight channel connector deployed to support an eight input depth electrode in an EEG procedure as depicted in FIG. 5A.

FIG. 5B shows a detailed illustration of the eight channel connector 510 deployed to support an eight input depth electrode 505 in an EEG procedure as depicted in FIG. 5A. As shown in FIG. 5B, the connector 510 is coupled to the depth electrode 505 through an electrical lead 506. In FIG. 5B, the intermediate connector 503 comprises a ring contact connector which is configured to receive a wire 516 with multiple ring contacts such that each ring contact is coupled to one of a plurality of inputs of the eight input depth electrode 505. The wire 516 comprises a set of ring contacts 509 such that as the wire 516 is inserted into the intermediate connector 503, each of these ring contacts 509 establishes an electrical contact with one of the eight ring shaped receptacles 503a in the intermediate connector 503. The electrical lead 506 comprises multiple conductors 518 inside it wherein each such conductor 518 acts as a separate electrical communication channel between the depth electrode 505 and eight channel connector 510. An exploded view of the lead 506 is shown as 506a which comprises eight different electrical conductors 518. As described above, the intermediate connector 503 uses ring contact receptacles and provides the system with greater flexibility in dealing with electrodes, such as the depth electrode 505. In some embodiments, connector 503 is used in different configurations.

Figure 6:
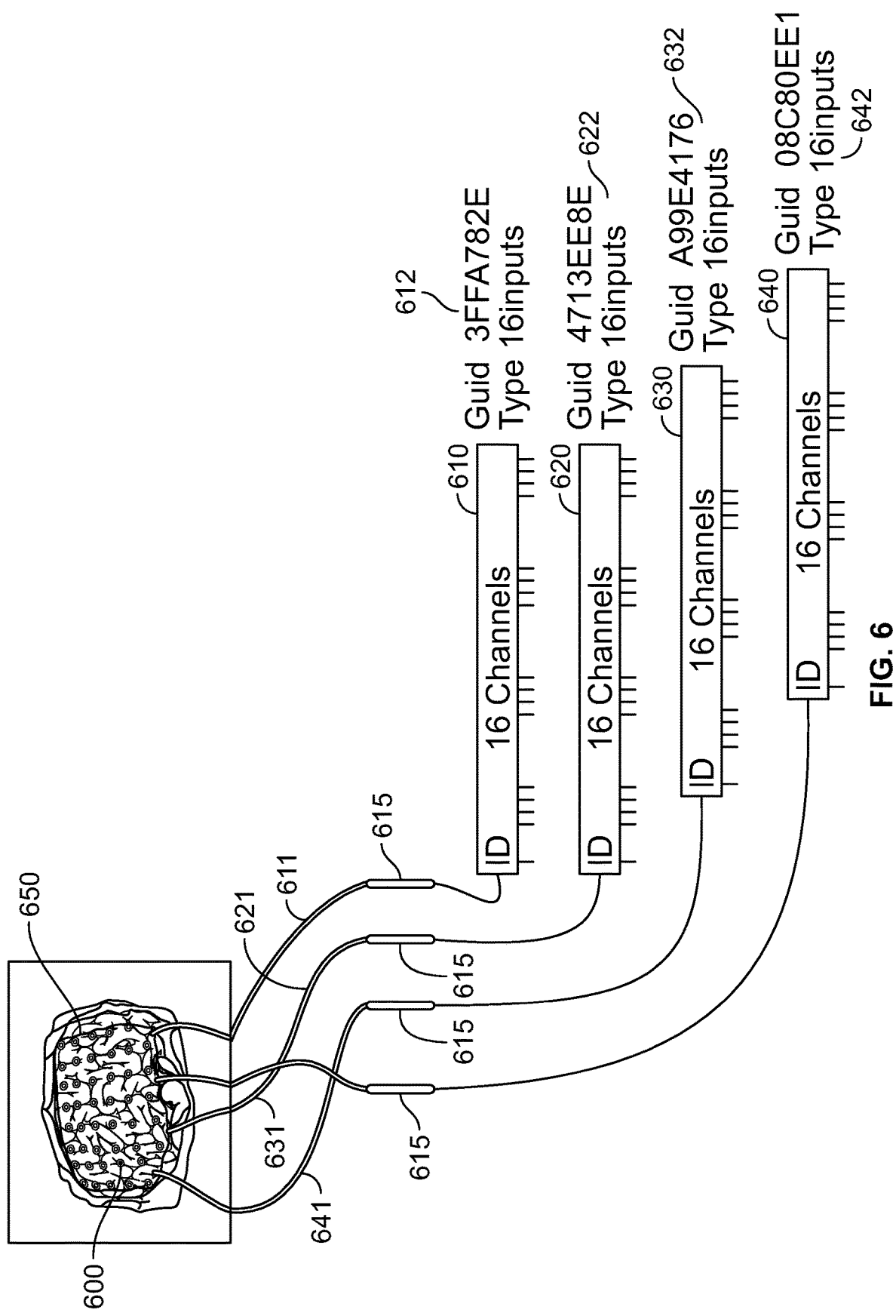
FIG. 6 shows a 64 electrode grid deployed on the brain using connectors in accordance with an embodiment of the present specification.

FIG. 6 shows a 64 electrode grid 600 deployed on a brain 650 using the connectors disclosed in this specification. As shown in FIG. 6, the electrode grid 600 comprises 64 electrodes which are deployed on various portions of the brain 650. The electrode grid 600 is deployed through an invasive surgery. The 64 electrodes are arranged in four groups with each group comprising 16 electrodes. The first group of 16 electrodes is coupled to a 16 channel connector 610 through a first electrical lead 611. The second group of 16 electrodes is coupled to a 16 channel connector 620 through a second electrical lead 621. The third group of 16 electrodes is coupled to a 16 channel connector 630 through a third electrical lead 631. The fourth group of 16 electrodes is coupled to a 16 channel connector 640 through a fourth electrical lead 641. In some embodiments, each lead 611, 621, 631, 641 is connected to its respective connector 610, 620, 630, 640 via an intermediate connector 615. The intermediate connectors 615 provide the system with greater flexibility when dealing with the limited geometry involved in surgical procedures. Each of the connectors 610, 620, 630 and 640 has a unique ID which is stored in an inbuilt memory in the corresponding connector. In an embodiment, the ID of various connectors comprises a 128 bit GUID which can be read by the system when the corresponding connector is plugged in a receiving socket of the system control device. Connector 610 comprises a first GUID 612, connector 620 comprises a second GUID 622, connector 630 comprises a third GUID 632 and connector 640 comprises a fourth GUID 642. When any of the connectors 610, 620, 630 and 640 is plugged in a receiving socket, the system reads its GUID information and establishes the identity of connector. Subsequently, the system configures itself to correlate or associate the electrodes mapped to the corresponding connector with the correct input channels.

In some embodiments, electrode identification is used to assist with co-registration between electrode location in the brain and identification of that electrode in volumetric data sets with MRI, CT, or other imaging studies. Co-registration enables rapid visualization of acquired data and EEG data (raw or analyzed) on the co-registered volumetric data set.

It should be appreciated that "co-registration" is an act of aligning in 3-D space specific data sets so they may be overlaid and viewed together. For example, CT and MRI images of the head and brain may be "co-registered" so both structural (CT) and soft tissue (MRI) data may be viewed in the same image. By using the ID of the electrode and associating it with a certain location where it was placed in/on the brain, a software application may be used to automatically detect which electrode in the image is associated with which data set being displayed on a review workstation (displaying EEG raw waveform data, for example) or may also be further analyzed such that, for example, seizure activity associated with a specific electrode may be displayed on a 3-D image as a color or intensity. To accomplish this, a general location of the electrode needs to be input by the user (for example, ID 12345678 was placed at coordinates X,Y,Z) and then the software application can locate potential matching electrodes in the image through image analysis and automatically assign electrode numbers (and associated waveform data).

In some embodiments, the systems and methods of the present specification provide stimulation and functional mapping tied to 3D visualization. Once an electrode location is identified in a 3-D image (for example could be a fused MRI CT image from the patient or a representative 3-D model of the skull and brain) then the electrode in the 3-D model may be clicked on and used as part of the software graphical user interface (GUI) to guide the process of cortical stimulation and functional mapping. Conventionally, these are cumbersome procedures involving a 2-D display showing multiple EEG waveforms and possibly moving leads on a "stimulator" used to deliver electrical current to the brain during the procedure.

The procedure itself is used to "map" portions of the brain to determine if it is safe to remove the section of the brain causing seizures or not. The basic steps, as known to persons of ordinary skill in the art comprise: a) using extra-cranial EEG (surface electrodes) perform a study to determine the approximate location within the brain where seizures occur, b) implant electrodes within or on the surface of the brain to improve the resolution of the recording, d) take patient off of medication to induce more seizures, e) record seizures and determine where the suspected location of the seizure source is, f) perform a functional mapping procedure if the source is close to an important location (such as, for example, motion, sensory, speech), and g) based upon the results of functional mapping, determine if the brain tissue causing the seizure may be removed or otherwise safely treated.

To perform the mapping, electrical current is passed between selected combinations of electrodes while specific tasks are performed by the patient, the results of which are recorded and analyzed. The electrical current (stimulation) has the effect of temporarily paralyzing the brain tissue between the electrodes emulating what the result would be if that brain tissue was removed. Normal function returns when the stimulation is stopped.

Since contemporary electrode placement techniques typically include combinations of sEEG (depth electrodes) and strip/grid (brain surface) electrodes, the prior art or conventional 2-D planar visualization problem (grid and strip electrodes on the surface of the brain) has become a more complex volumetric problem. Volumetric visualization enables an operator to know how to stimulate between two sets of electrodes in the brain, where in the brain should the stimulation be applied and the ability to have the system easily, rapidly, and accurately associate electrodes found in an image with the actual EEG data coming from the electrode (or cortical stimulation provided through it). Having the electrode ID known to the system enables automatic association in 3-D images of electrode to data.

Accordingly, in one embodiment, the system generates a three dimensional image having a plurality of electrodes associated with pixel positions in three dimensional image. The system further provides a graphical user interface configured to receive a user input designating at least one of the plurality of pixel positions in the three dimensional image. Upon receiving the user input designating at least one of the plurality of pixel positions, the system determines the electrode associated with selected pixel position and accesses the unique identification code associated with the determined electrode. The system then uses the unique identification code to access data, stored in a local or remote memory, to acquire data associated with the unique identification code and, therefore, with the selected electrode. It should be appreciated that, in one embodiment, the system stores electrode-specific data in association with a unique identification code and further stores associations of the unique identification with particular electrodes.

Figure 7:
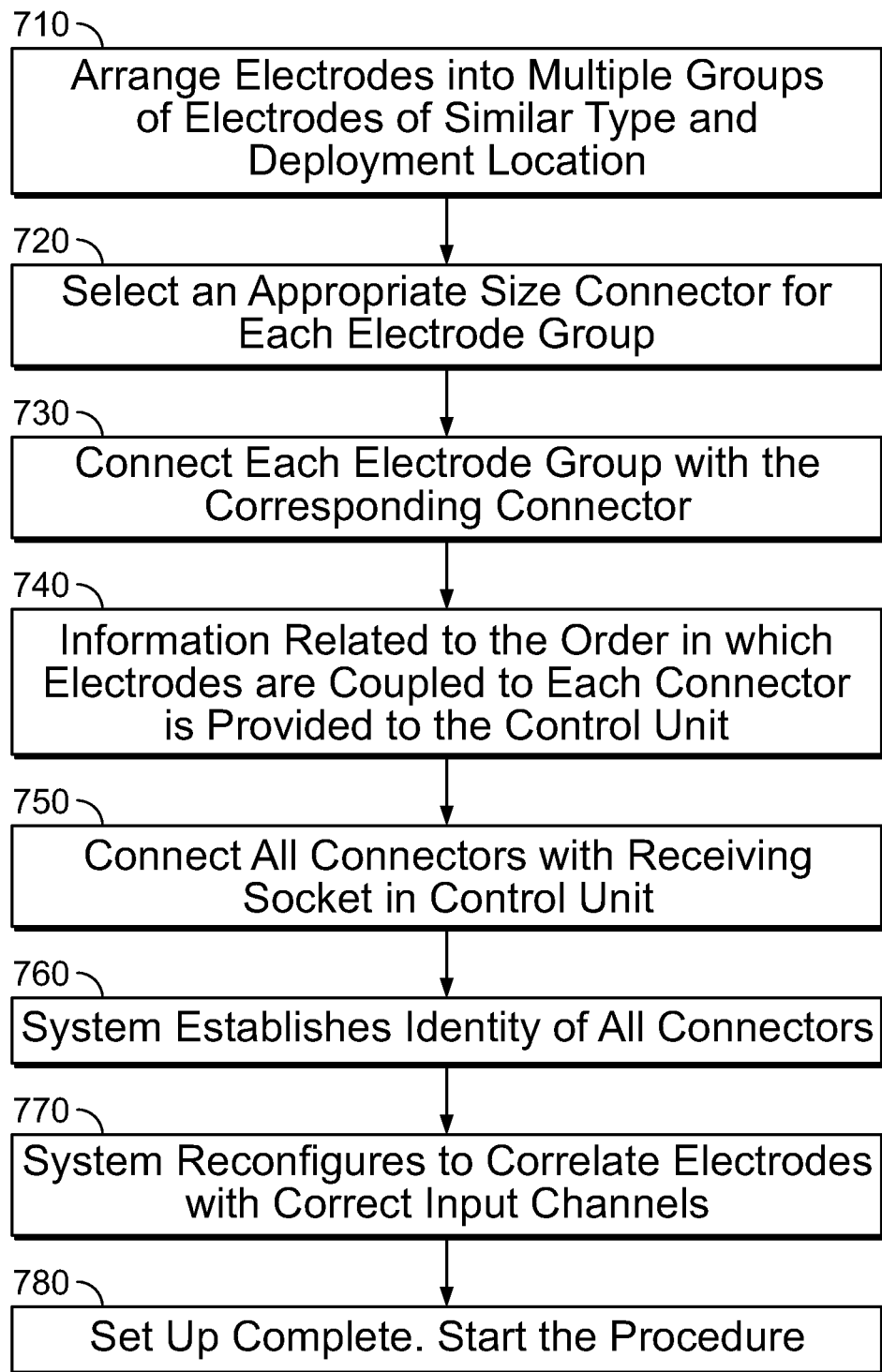
FIG. 7 shows a flowchart illustrating the steps performed in a method of configuring an electrode connection system in accordance with one embodiment of the present specification.

FIG. 7 shows a flowchart illustrating the steps involved in one embodiment of configuring a system using the connectors disclosed in the present specification. As shown in FIG. 7, at step 710, the electrodes are arranged into a plurality of groups such that electrodes of similar type and deployment location are included in the same group. The electrodes in the same group have similarities in terms of their input channel and positioning and are coupled to the same connector in a specific sequence.

At step 720, based on the number of electrodes in each group, a connector of appropriate size is selected for each electrode group. The connector should have a number of input channels greater than or equal to the number of electrodes in the electrode group supported by it. At step 730, electrodes are connected with the corresponding connectors. At step 740, the information related to the order in which the electrodes are coupled to each connector is provided to the control unit. At step 750, the connectors are connected with a receiving socket in the control unit of the medical device. At step 760, the system establishes the identity of all connectors using the unique ID information stored in each connector. At step 770, the system configures itself to correlate or associate each electrode with its corresponding input channel in the control unit. At step 780, the system set up is complete and procedure can be started. In some embodiments, step 740 is executed after step 750 when the system requests for information about the electrode group coupled with a connector at a run time after a connector is inserted in the receiving socket and the user subsequently provides this information to the control unit.

Figure 8A:
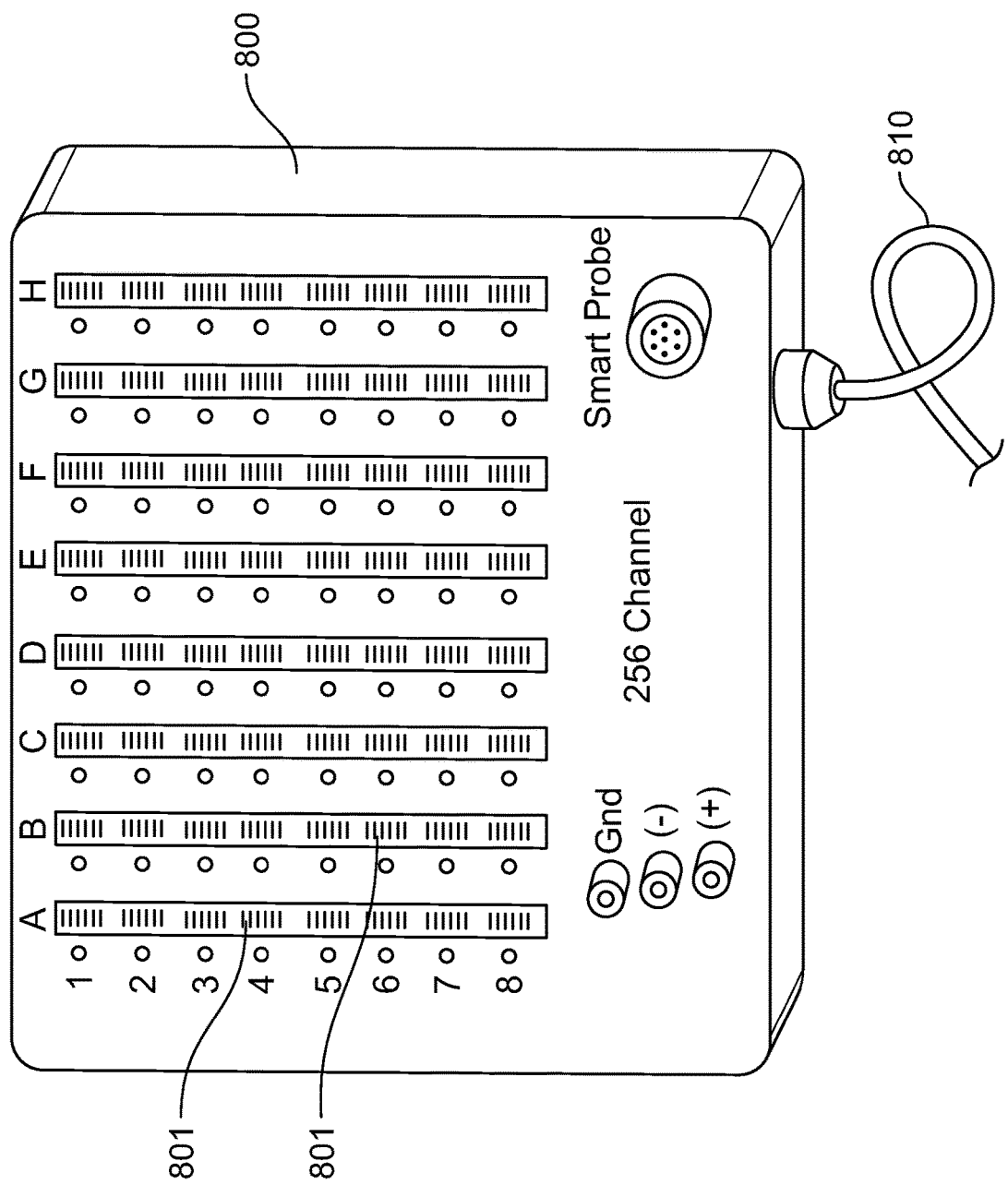
FIG. 8A shows a control unit of a 256 channel neuromonitoring and neurodiagnostics EEG system having receiving sockets which are configured to receive multiple connectors, in accordance with an embodiment of the present specification.
Figure 8B:
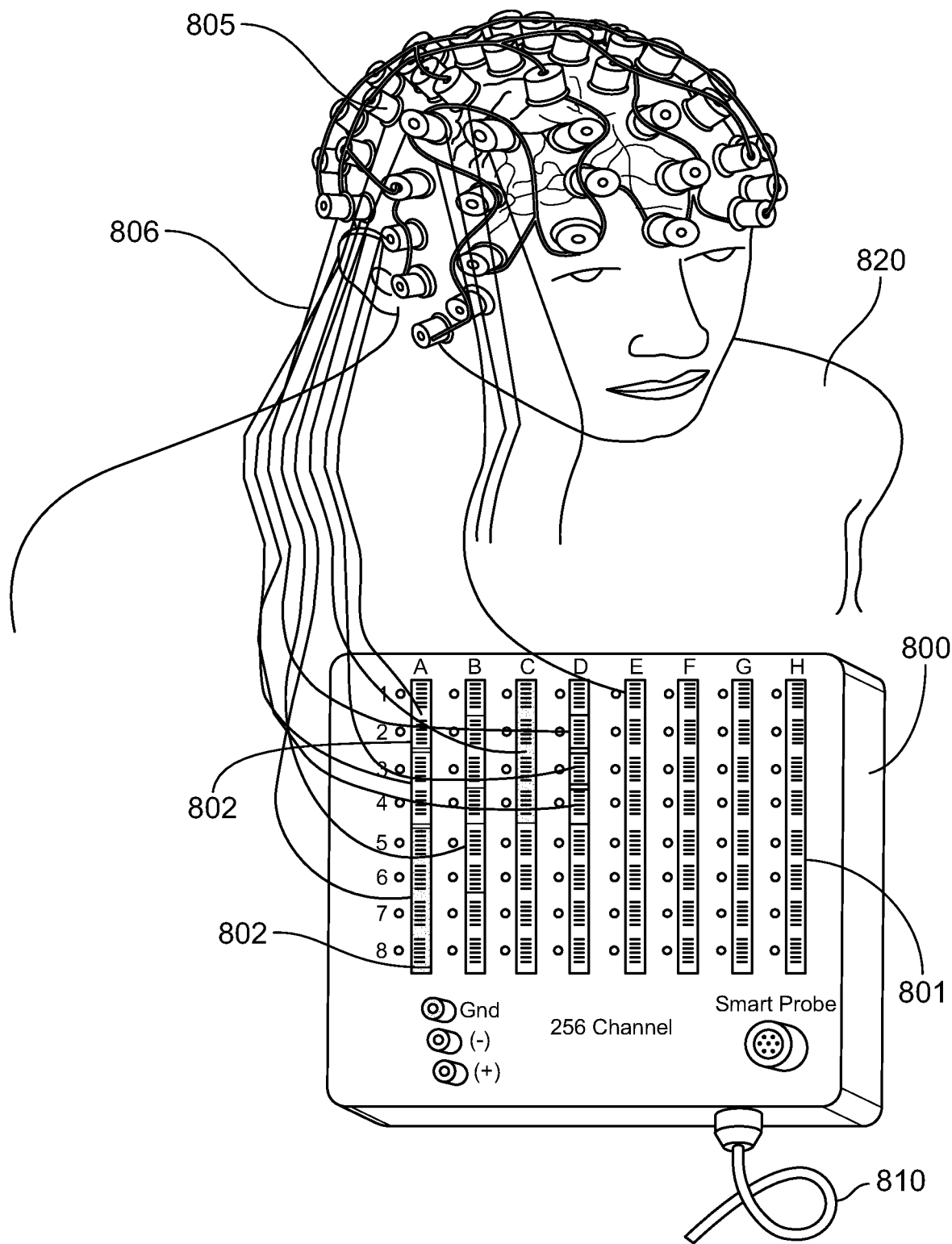
FIG. 8B shows the system of FIG. 8A being used for monitoring the neurological state a patient.

FIG. 8A shows a control unit 800 of a 256 channel neuromonitoring and neurodiagnostics EEG system having receiving sockets 801 which are configured to receive multiple connectors. As shown in FIG. 8A, the control unit 800 of the medical system comprises a plurality of receiving sockets 801. The control unit 800 comprises 256 input channels and can therefore support the same number of electrodes. In control unit 800, the receiving sockets 801 corresponding to the 256 input channels are divided into eight columns such that each column corresponds to 32 input channels. The control unit 800 is coupled to a data acquisition system through cable 810. FIG. 8B shows the medical system of FIG. 8A being used for monitoring the neurological state of a patient. As shown in FIG. 8B, a plurality of electrodes 805 are positioned over the head of a patient 820 to monitor the electrical activity of brain. The electrodes 805 are arranged into groups such that each group comprises electrodes of same type. These multiple groups of electrodes are coupled to separate connectors, such as the connectors 410, 420, 430, and 440 shown in FIG. 4. The electrodes 805 are coupled to connectors 802 though a plurality of electrical leads 806. The connectors 802 are coupled to the receiving sockets 801 as shown in FIG. 8B. Each of the connectors 802 has a unique identity which is stored in the connector in the form of a GUID. The receiving sockets 801 are configured to read the GUID information of each connector and establish its identity. After establishing the identity of connectors 802, the control unit 800 configures the system to correlate or associate each of the electrodes 805 with its corresponding input channel in the control unit 800.

In some embodiments, the system provides an automatic 'sanity' check to verify that the type and configuration of electrode connected, particularly a grid electrode, is what the operator assigned. In some embodiments, the system performs checks to confirm the electrode is connected, that it is the correct electrode, and to confirm the electrode shape and configuration. U.S. Patent Provisional Application No. 62/758,320, also by the Applicant of the present specification, is herein incorporated by reference in its entirety.

For example, an 8×8 grid electrode has 4 leads coming off of it, each lead carrying signals from 16 electrodes within one (4×4) quadrant of the grid. Each lead is connected to a single connector having an associated unique ID. As each connector is attached to the amplifier, the user needs to identify a) whether it is part of the 8×8 grid and b) what quadrant it represents. In accordance with some aspects of the present specification, the system provides safety or sanity check that can be performed automatically by the system once all of the connections have been made. The system will know that it is an 8×8 grid and the user assigned quadrants for each 4×4 connector within the grid, and can use this information to verify that the association was performed correctly.

In some embodiments, such as that of FIG. 3E, each lead coming directly from the electrode (and preferably created at the time of manufacture) includes a unique ID that is passed through directly to the amplifier. In this case, there is no user association needed to assign the connector to a specific quadrant or to even determine that it is an 8×8 grid as that would be automatic, but the system still performs the sanity check to ensure labeling from the manufacturer is correct.

Once connected and assigned, the system analyzes impedance, waveform, and stimulation data to assess if the operator has performed the association correctly. In some embodiments, the system measures impedance to determine if an electrode is connected. Based on the impedance measurements, the system removes traces for the electrode and/or generates a warning to the user if the electrode is not detected. In one embodiment, an 8×8 electrode array includes four 16 conductor pigtail connectors attached to it and existing a patient's skull. Each pigtail connector needs to be connected to a GUID by an operator and assigned a grid type/location by the operator (assuming no other means of auto ID has been implemented, such as the pigtail ID tag described above). Once all four pigtails have been assigned to a quadrant of the 8×8 array, a software application of the system determines if the signals "make sense" for that specific configuration and if not, a warning indicator is presented to the operator. For example, in an embodiment, a software application of the system verifies the shape and function of an electrode by stimulating and recording on all channels, then reverse calculating the geometry to verify it matches what the system believes is connected. In some embodiments, the system prompts the user when it detects an unknown connector is attached to the system.

In various embodiments, the connectors and receiving sockets of the systems of the present specification are 'keyed' in such a way so that the connectors can be inserted into the receiving sockets at several locations, but cannot be inserted backwards or at an invalid location. For example, in some embodiments, a connector is configured such that it can be inserted in a top-up or bottom-up orientation, with respect to its horizontal axis, into a receiving socket, but only at discrete locations in the receiving socket. In an embodiment, the receiving socket is configured to detect the orientation of the connector and the ID of the connector. In another embodiment, the pins are duplicated on both top and bottom sides of the connector. Some embodiments of keyed connector and receiving socket connections are described with reference to FIGS. 9A through 11 below and are intended to be exemplary in nature and not limiting with respect to the present specification.

Figure 9A:
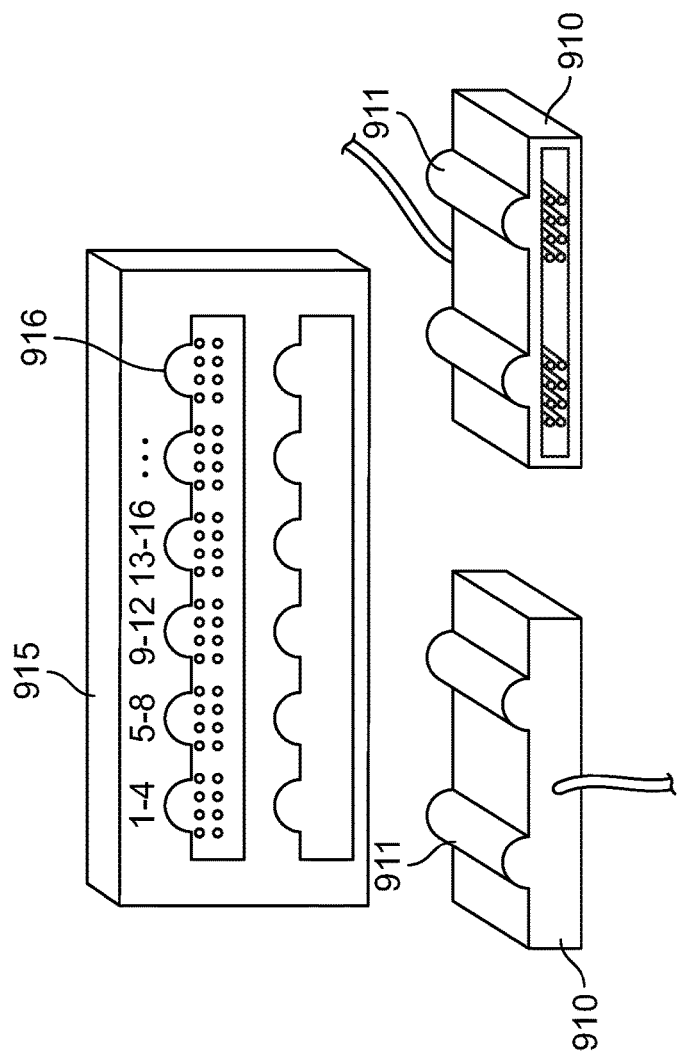
FIG. 9A shows an illustration of an exemplary connector and receiving socket in accordance with various embodiments of the present specification.
Figure 9B:
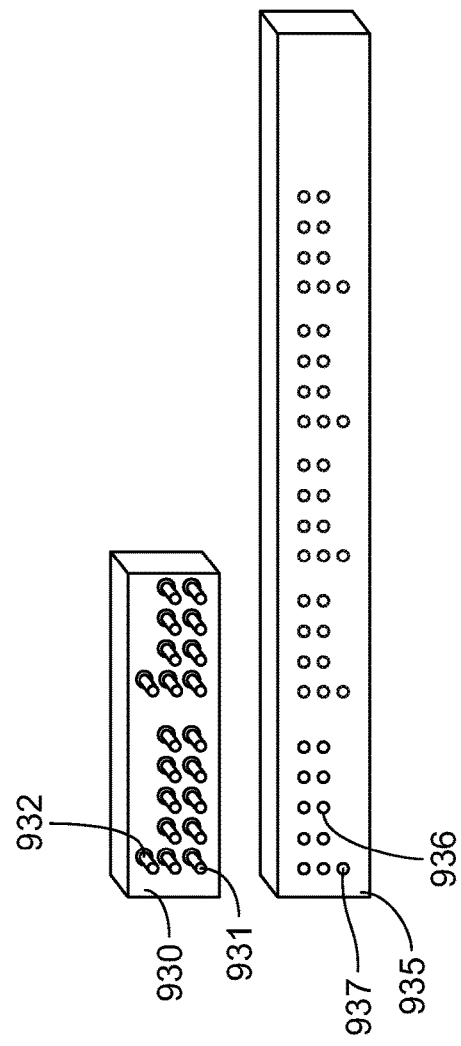
FIG. 9B shows another illustration of an exemplary connector and receiving socket in accordance with other embodiments of the present specification.

FIG. 9A and FIG. 9B show an illustration of exemplary embodiments of connectors 910, 930 and receiving sockets 915, 935. The connectors 910, 930 and receiving sockets 915, 935 are configured with design features to allow for only one orientation during connection. Referring to FIG. 9A, connector 910 includes a pair of 'keys' or ridges 911 at its top surface with align with notches 916 in the receiving socket 915 to ensure the connector 910 is inserted correctly into the receiving socket 915. In embodiments, the connector 910 has one design element, such as the ridge 911, for every four signal input pins and the receiving socket 915 has multiple notches, such as the notch 916, such that the connector 910 can be received at multiple locations along the receiving socket 915 occupying 4, 8, 12, or 16 input sockets. In the above embodiment, the connector 910 comprises one design element or ridge 911 and the receiving socket has one notch 916 for every four number of signal input pins. In other embodiments, the number of signal input pins corresponding to each design element or ridge 911 is of a different multiple, for example, 5, 6, or 7, and the notch 916 of the receiving socket 915 is configured accordingly to support the corresponding structure of the connector 910.

Referring to FIG. 9B, the connector 930 is provided with an asymmetric distribution of pins 931 which corresponds with a matching asymmetric distribution of receptacles 936 on the receiving socket 935 to ensure the connector 930 is inserted correctly into the receiving socket 935. As depicted in FIG. 9B, an ID output pin 932 on the connector 930 is positioned separate from the set of pins 931 and aligns with an ID input socket 937 separate from the set of receptacles 936 on the receiving socket 935 to ensure proper alignment and identification.

Figure 10:
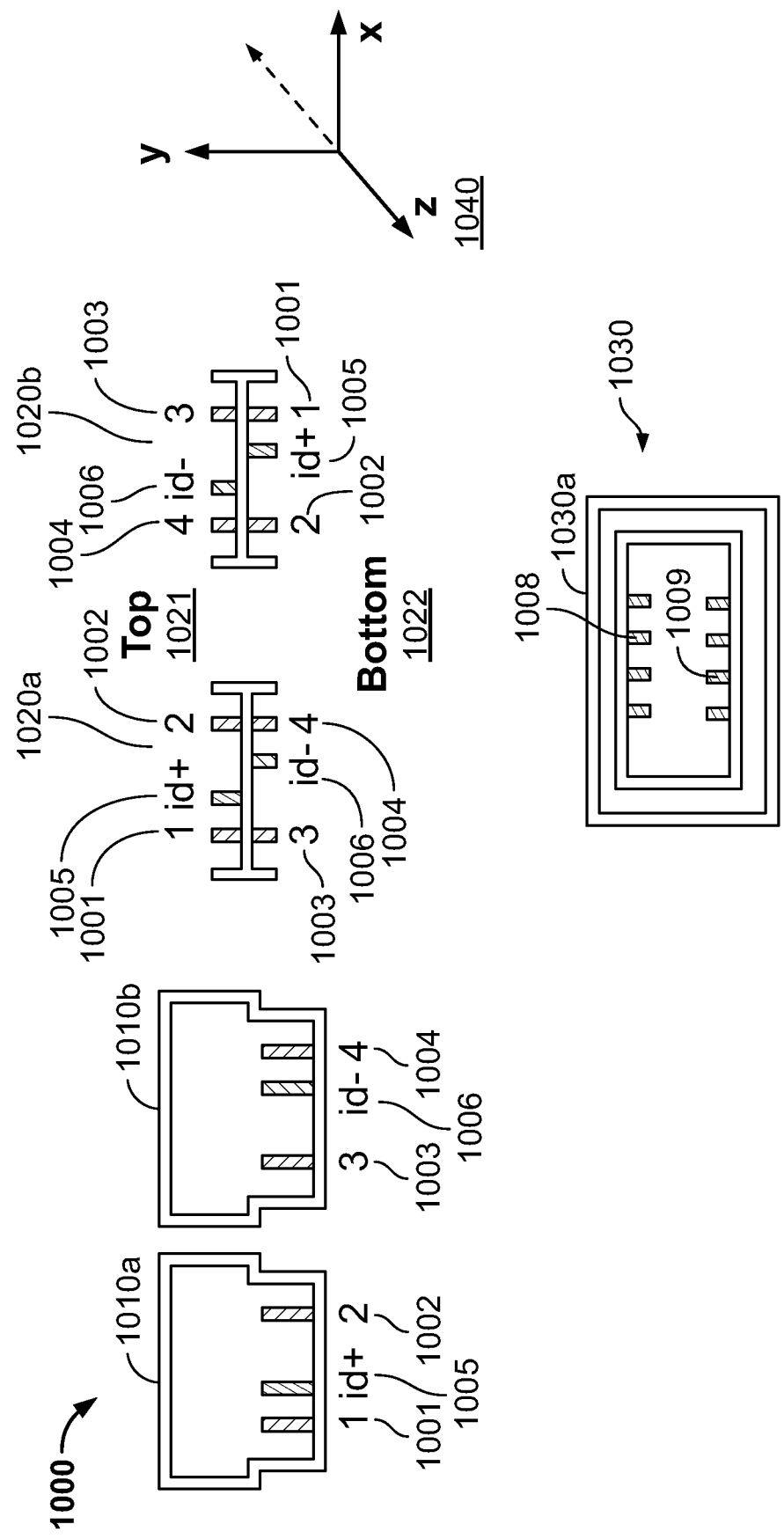
FIG. 10 illustrates a connector which can be used in dual orientations in accordance with an embodiment of the present specification.

FIG. 10 illustrates a connector 1000 which can be used in dual orientations in accordance with an embodiment of the present specification. A first side 1010a and a second side 1010b of a connector 1000 are depicted in FIG. 10. In an exemplary embodiment, the connector 1000 comprises four output signal pins 1001, 1002, 1003 and 1004 and two ID pins 1005 and 1006. The first side 1010a comprises the output signal pins 1001 and 1002 and the ID pin 1005. The second side 1010b comprises the output signal pins 1003 and 1004 and the ID pin 1006.

The connector 1000 can be coupled to the receiving unit or socket 1030 in two different orientations. A first front-on view 1020a depicts the first side 1010a of the connector 1000 oriented to a 'top' surface 1021 and the second side 1010b oriented to a 'bottom' surface 1022. View 1020a of the connector 1000 depicts the positioning of the various output signal pins and the ID pins in a first orientation, with output signal pins 1001 and 1002 and ID pin 1005 positioned on said 'top' surface 1021 and output signal pins 1003 and 1004 and ID pin 1006 positioned on said 'bottom' surface 1022. A second front-on view 1020b depicts the second side 1010b of the connector 1000 oriented to said 'top' surface 1021 and the first side 1010a oriented to said 'bottom' surface 1022. View 1020b depicts the positioning of the various output signal pins and the ID pins in a second orientation, with output signal pins 1003 and 1004 and ID pin 1006 positioned on said 'top' surface 1021 and output signal pins 1001 and 1002 and ID pin 1005 positioned on said 'bottom' surface 1022. In the second view 1020b, the connector 1000 is rotated 180 degrees about its horizontal axis or Z axis 1040 as compared to its position in the first view 1020a.

As shown in FIG. 10, the first and the second views 1020a, 1020b of connector 100, respectively depicting first and second configurations, are horizontally flipped images of each other, about the Z axis 1040, and hence it is not possible to distinguish one orientation from another from the physical structure. In the disclosed system, the receiving unit 1030 detects the orientation of the connector 1000 based on the polarities of the ID pins. In FIG. 10, the two ID pins 1005, 1006 have opposite polarities such that ID pin 1005 has a positive polarity and ID pin 1006 has a negative polarity. In other embodiments, ID pin 1005 has the negative polarity and ID pin 1006 has the positive polarity. When the connector 1000 is inserted in the receiving unit 1030, depicted in a front-on view 1030a, the various output signal pins and the ID pins of the connector 1000 establish contact with the various input mating sockets or pins in the receiving unit 1030. When the connector 1000 is inserted in the receiving unit 1030 in the first orientation, as shown in view 1020a, the ID pin 1005 establishes contact with the ID input pin 1008 and the ID pin 1006 establishes contact with the ID input pin 1009 of the receiving unit 1030. Alternatively, when the connector 1000 is inserted in the receiving unit 1030 in the second orientation, as shown in view 1020b, the ID pin 1006 establishes contact with the ID input pin 1008 and the ID pin 1005 establishes contact with the ID input pin 1009 of the receiving unit 1030. The system reads the respective polarities of the ID pins in contact with the ID inputs sockets 1008 and 1009 and hence detects the orientation of the connector 1000 as inserted in the receiving socket 1030. Subsequently, the system reconfigures itself to automatically map each input with its corresponding input channel.

The system disclosed in FIG. 10 uses two ID pins with opposite polarities. In some embodiments, the polarities of the two ID pins are not opposite and the two ID pins are just maintained at different voltage levels and the identity of the ID pins is detected based on the signal/voltage received from the corresponding ID pins. Once the system identifies and distinguishes the two ID pins, the orientation of the connector as inserted in the receiving socket is detected. The system disclosed in FIG. 10 comprises four output signal pins, however, in other embodiments, the number of output signal pins present in the connector is different, such as less than 4 or greater than 4, including 5, 6, 7, or more.

Figure 11:
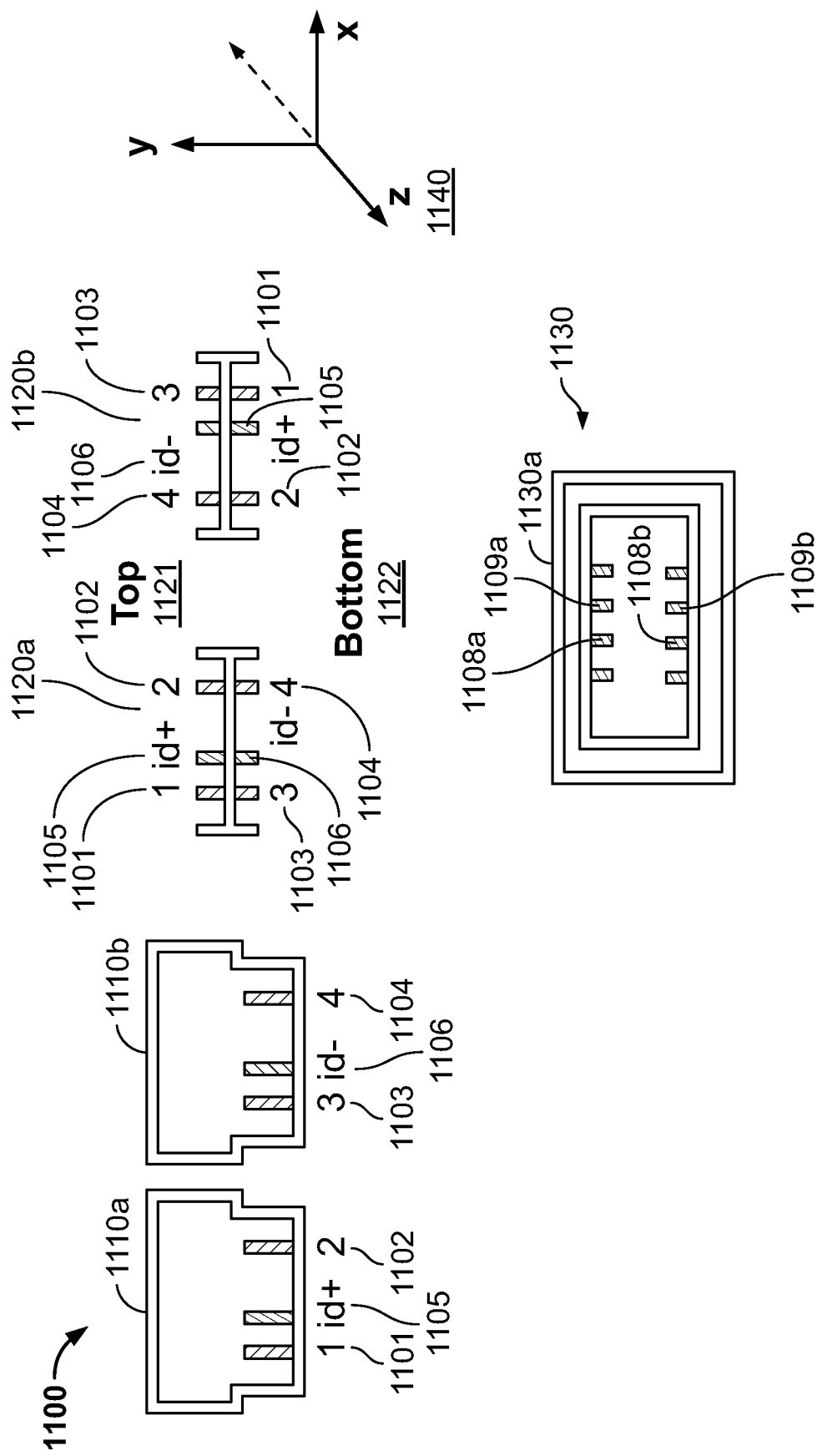
FIG. 11 illustrates a connector which can be used in dual orientations in accordance with another embodiment of the present specification.

FIG. 11 illustrates a connector 1100 which can be used in dual orientations in accordance with another embodiment of the present specification. A first side 1110a and a second side 1110b of a connector 1100 are depicted in FIG. 11. The connector 1100 comprises four output signal pins 1101, 1102, 1103 and 1104 and two ID pins 1105 and 1106. The first side 1110a comprises the output signal pins 1101 and 1102 and the ID pin 1105. The second side 1110b comprises the output signal pins 1103 and 1104 and the ID pin 1106.

The connector 1100 can be coupled to the receiving unit or socket 1130 in two different orientations. A first front-on view 1120a depicts the first side 1110a of the connector 1100 oriented to a 'top' surface 1121 and the second side 1110b oriented to a 'bottom' surface 1122. View 1120a of the connector 1100 depicts the positioning of the various output signal pins and the ID pins in a first orientation, with output signal pins 1101 and 1102 and ID pin 1105 positioned on said 'top' surface 1121 and output signal pins 1103 and 1104 and ID pin 1106 positioned on said 'bottom' surface 1122. A second front-on view 1120b depicts the second side 1110b of the connector 1100 oriented to said 'top' surface 1121 and the first side 1110a oriented to said 'bottom' surface 1122. View 1120b depicts the positioning of the various output signal pins and the ID pins in a second orientation, with output signal pins 1103 and 1104 and ID pin 1106 positioned on said 'top' surface 1121 and output signal pins 1101 and 1102 and ID pin 1105 positioned on said 'bottom' surface 1122. In the second view 1120b, the connector 1100 is rotated 180 degrees about its horizontal axis or Z axis 1140 as compared to its position in the first view 1120a.

When the connector 1100 is inserted in the receiving unit 1130, the various output signal pins and the ID pins of the connector 1100 establish contact with the various mating sockets or pins in the receiving unit 1130. In the system disclosed in FIG. 11, the receiving unit 1130, shown in a front-on view 1130a, detects the orientation of the connector 1100 based on the location of the ID pins 1105 and 1106. When the connector 1100 is inserted in the receiving unit 1130 in the first orientation, as shown in view 1120a, the ID pin 1105 establishes contact with the ID input pin 1109a and the ID pin 1106 establishes contact with the ID input pin 1109b of the receiving unit 1130. Alternatively, when the connector 1100 is inserted in the receiving unit 1030 in the second orientation, as shown in view 1120b, the ID pin 1105 establishes contact with the ID input pin 1108a and the ID pin 1106 establishes contact with the ID input pin 1108b of the receiving unit 1130. The system verifies the positions of the ID pins 1105 and 1106 and detects the orientation of the connector 1100 as inserted in the receiving socket 1130 based on these positions. Subsequently, the system reconfigures itself to automatically map each input with its corresponding input channel.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in neuromonitoring and neurodiagnostics procedures may be applied to systems, devices, and methods to be used in other types of medical procedures for monitoring or treatment of diseases.

Variations and modifications will occur to those of skill in the art after reviewing this disclosure. The disclosed features may be implemented, in any combination and sub-combination (including multiple dependent combinations and sub-combinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A system for neuromonitoring comprising:
 a plurality of electrode groups, wherein each group of the plurality of electrode groups comprises electrodes, wherein each of the electrodes in each group has at least one of a similar monitoring functionality type or a similar deployment location and wherein each of the plurality of electrode groups has at least one electrode group lead;
 a plurality of connectors, wherein each of the at least one electrode group leads is coupled to at least one connector of the plurality of connectors and wherein each of the electrode group leads and/or each of connectors of the plurality of connectors are electronically associated with a unique identification code; and,
 a control unit comprising at least one receiving unit configured for receiving the plurality of connectors, wherein the control unit is configured to determine at least one of the unique identification code of each connector of the plurality of connectors or the unique identification code of each of the at least one electrode group leads and to associate each electrode in the plurality of electrode groups with a corresponding input channel in the control unit based on at least one of the unique identification code of each connector or the unique identification code of each of the at least one electrode group leads.

2. The system of claim 1, wherein said unique identification code is in a 128 bit GUID format.

3. The system of claim 1, wherein said at least one receiving unit comprises a plurality of input sockets configured to receive one or more connectors of said plurality of connectors.

4. The system of claim 3, wherein said one or more connectors are configured to be coupled to any of the plurality of input sockets of said at least one receiving unit.

5. The system of claim 1, wherein the control unit is configured to determine at least one of the unique identification code of each connector of the plurality of connectors or the unique identification code of each of the at least one electrode group leads by receiving, via each connector of the plurality of connectors, data indicative of at least one of the unique identification code of each connector of the plurality of connectors or the unique identification code of each of the at least one electrode group leads.

6. The system of claim 1, wherein the control unit is configured to receive, via each connector of the plurality of connectors, data indicative of at least one of the unique identification code of each connector of the plurality of connectors or the unique identification code of each of the at least one electrode group leads through a direct pin-to-pin electrical pass through.

7. The system of claim 1, wherein the control unit is configured to determine at least one of the unique identification code of each connector of the plurality of connectors or the unique identification code of each of the at least one electrode group leads by receiving, via at least one connector of the plurality of connectors, data indicative of at least one of the unique identification code of each connector of the plurality of connectors or the unique identification code of each of the at least one electrode group leads.

8. The system of claim 1, wherein the control unit is configured to receive, via each connector of the plurality of connectors, data indicative of at least one of a production date or authentication data.

9. The system of claim 1, wherein the control unit is configured to receive, via each connector of the plurality of connectors and through a direct pin-to-pin electrical pass through, data indicative of at least one of a production date of the plurality of connectors or the electrodes or authentication data.

10. The system of claim 1 wherein said connector has a designated output pin which is configured to transmit information related to the unique identification code to said control unit.

11. The system of claim 10, wherein data indicative of the unique identification code is stored in a memory associated with the designated output pin.

12. The system of claim 1, wherein data indicative of the unique identification code comprises a bar code or a radio frequency code (RFID).

13. The system of claim 1, wherein data indicative of the unique identification code is stored using at least one pin configured as at least one dip switch comprising at least one resistor.

14. The system of claim 1, wherein each connector of the plurality of connectors is configured to be inserted in the at least one receiving unit in at least two different orientations.

15. The system of claim 1, wherein each connector of the plurality of connectors comprises at least two designated output pins, each of which being configured to convey data indicative of the unique identification code and an orientation of a connector of the plurality of connectors.

16. The system of claim 15, wherein the at least two designated output pins are configured to be at different polarities or at different voltage levels to indicate the orientation of the connector of the plurality of connectors.

17. The system of claim 15, wherein a physical position of the at least two designated output pins is different in each of the at least two different orientations.

18. The system of claim 1, further comprising a rigid connector plate, wherein the connector plate comprises a plurality of openings, each opening of the plurality of openings being configured to receive each connector of the plurality of connectors, and wherein each opening of the plurality of openings is separated from an adjacent opening of the plurality of openings by a portion of the connector plate.

19. The system of claim 18, wherein each connector of the plurality of connectors is partially positioned in each opening of the plurality of openings such that a first end of each connector extends outward from a first surface of the connector plate and a second end, opposing the first end, of each connector extends outward from a second surface of the connector plate, wherein the second surface opposes the first surface.

20. The system of claim 1, further comprising a rigid connector plate, wherein the connector plate comprises a plurality of sockets, each socket of the plurality of sockets being configured to receive each connector of the plurality of connectors, and wherein each socket of the plurality of sockets is separated from an adjacent socket of the plurality of sockets by a portion of the connector plate and is configured to electrically connect to a corresponding socket in the at least one receiving unit.

21. The system of claim 1, wherein the control unit is further configured to determine at least one of authentication data or data indicative of a production date of the plurality of connectors or the electrodes by receiving, via at least one connector of the plurality of connectors, data indicative of the at least one of authentication data or data indicative of the production dates of the plurality of connectors or the electrodes.

22. The system of claim 1, wherein the control unit is configured to generate data indicative of, or associated with, a three-dimensional image.

23. The system of claim 22, wherein the three-dimensional image comprises a plurality of pixel positions and wherein at least one of the plurality of pixel positions is associated, in a memory, with at least one of the electrodes.

24. The system of claim 23, wherein the control unit is configured to receive data indicative of a user input selecting at least one of the plurality of pixel positions of the three-dimensional image and is configured to identify at least one electrode associated with the selected at least one of the plurality of pixel positions based on the user input.

25. The system of claim 24, wherein the control unit is further configured to determine data associated with the identified at least one electrode by using the unique identification code associated with the at least one electrode.

26. The system of claim 1, wherein the control unit is configured to automatically populate at least one graphical user interface with data indicative representative of each of the electrodes based on the unique identification codes.

27. The system of claim 26, wherein the control unit is configured to automatically update data displayed in the at least one graphical user interface with updated data indicative representative of each of the electrodes based on the unique identification codes after one or more of the electrodes is moved or disconnected and reconnected to the at least one receiving unit.

28. The system of claim 1, wherein the control unit is configured to receive data indicative of a user selection of a trace displayed on a graphical user interface, wherein, upon receiving data indicative of the user selection of the trace, the control unit is configured to trigger a visual indicator positioned in physical proximity to or association with one of the electrodes that acquired data associated with said trace.

29. The system of claim 28, wherein the visual indicator is at least one of a light positioned on the one of the electrodes, a light positioned on a connector of the plurality of connectors in data communication with the one of the electrodes, or a light positioned on a lead attached to the one of the electrodes.

30. The system of claim 1 wherein said electrodes are configured in groups of 4, 5, 6, 7, 8, 9, 10, 11, 12, 13, 14, 15 or 16 electrodes.

31. The system of claim 1 wherein said system is configured to perform at least one of an electroencephalography, electrocardiogram, electromyography, polysomnography, or intraoperative neural monitoring procedure.

32. The system of claim 1, wherein the unique identification code associated with each said electrode group lead is stored in association with each electrode group lead, and wherein the unique identification code is configured as any one of a crimp, an adhesive label or an embedded code on each electrode group lead.

33. The system of claim 1, wherein each connector of the plurality of connectors further comprises a value and wherein the value is representative of a number of permissible uses of the connector of the plurality of connectors.

34. The system of claim 33, wherein the value is indicative of a maximum number of sterilization cycles of the connector of the plurality of connectors and wherein the maximum number of sterilization cycles is equal to, or less than, 20.

35. The system of claim 1, wherein the control unit is configured to access a value associated with each connector of the plurality of connectors, wherein the value is indicative of a maximum number of sterilization cycles of the connector of the plurality of connectors and wherein the maximum number of sterilization cycles is equal to, or less than, 20.

* * * * *